(12) United States Patent
Ewing et al.

(10) Patent No.: US 8,030,306 B2
(45) Date of Patent: Oct. 4, 2011

(54) AZABICYCLIC HETEROCYCLES AS CANNABINOID RECEPTOR MODULATORS

(75) Inventors: William R. Ewing, Yardley, PA (US); Yeheng Zhu, Stockton, NJ (US); Richard B. Sulsky, West Trenton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 6 days.

(21) Appl. No.: 12/518,707

(22) PCT Filed: Dec. 13, 2007

(86) PCT No.: PCT/US2007/087404
§ 371 (c)(1),
(2), (4) Date: Sep. 15, 2009

(87) PCT Pub. No.: WO2008/076810
PCT Pub. Date: Jun. 26, 2008

(65) Prior Publication Data
US 2010/0029656 A1  Feb. 4, 2010

Related U.S. Application Data

(60) Provisional application No. 60/869,933, filed on Dec. 14, 2006.

(51) Int. Cl.
*C07D 487/04* (2006.01)
*A61K 31/5025* (2006.01)
*A61P 3/00* (2006.01)

(52) U.S. Cl. ........................ 514/248; 544/236

(58) Field of Classification Search .......... 544/263, 544/236; 514/248
See application file for complete search history.

(56) References Cited

U.S. PATENT DOCUMENTS

| 7,629,342 B2 * | 12/2009 | Ewing et al. ............ 514/252.01 |
| 7,777,036 B2 * | 8/2010 | Kamboj et al. ............... 544/367 |
| 2005/0171110 A1 | 8/2005 | Yu et al. |
| 2010/0216848 A1 * | 8/2010 | Peresypkin et al. ......... 514/351 |

FOREIGN PATENT DOCUMENTS

| WO | WO 2005/063762 | 7/2005 |
| WO | WO 2005063762 | * 7/2005 |
| WO | WO 2006/138682 | 12/2006 |

* cited by examiner

*Primary Examiner* — James O Wilson
*Assistant Examiner* — Cecilia M Jaisle
(74) *Attorney, Agent, or Firm* — Ying Wang

(57) ABSTRACT

The present application describes CB-1 inverse agonists according to Formula (I) and (Ia), pharmaceutical compositions comprising at least one compound according to Formula (I) or (Ia), and optionally one or more additional therapeutic agents and methods of treatment using the compounds according to Formula (I) or (Ia), both alone and in combination with one or more additional therapeutic agents. The preferred compounds have the general Formula (Ia), including all prodrugs, pharmaceutically acceptable salts and stereoisomer, thereof, wherein $R_1$, $R_2$, $Ar_1$, $Ar_2$ are defined herein.

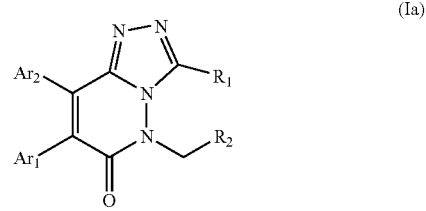

(Ia)

13 Claims, No Drawings

AZABICYCLIC HETEROCYCLES AS CANNABINOID RECEPTOR MODULATORS

This application claims priority to US Provisional Application No. 60/869,933, filed on Dec. 14, 2006, which is referenced herein in its entirety.

Compounds of the present invention demonstrate unexpected combination of high CB-1 inverse agonist activity and a short canine half-life or have increased aqueous solubility of >1 μg/mL achieved by the combination of appropriate $Ar_1$, $Ar_2$ and $R_1$ The compounds of the instant invention preferably have CB-1 Ki values of 0.5 nM-20 nM with and canine half-life values of <50 hrs or have increased aqueous solubility of >1 μg/mL.

BACKGROUND

Delta-9-tetrahydrocannabinol or Delta-9 THC, the principle active component of Cannabis sativa (marijuana), is a member of a large family of lipophilic compounds (i.e., cannabinoids) that mediate physiological and psychotropic effects including regulation of appetite, immunosuppression, analgesia, inflammation, emesis, anti-nocioception, sedation, and intraocular pressure. Other members of the cannabinoid family include the endogenous (arachidonic acid-derived) ligands, anandamide, 2-arachidonyl glycerol, and 2-arachidonyl glycerol ether. Cannabinoids work through selective binding to and activation of G-protein coupled cannabinoid receptors. Two types of cannabinoid receptors have been cloned including CB-1 (L. A. Matsuda, et al., *Nature*, 346, 561-564 (1990)), and CB-2 (S. Munro, et al., *Nature*, 365, 61-65 (1993)). The CB-1 receptor is highly expressed in the central and peripheral nervous systems (M. Glass, ct al., *Neuroscience*, 77, 299-318 (1997)), while the CB-2 receptor is highly expressed in immune tissue, particularly in spleen and tonsils. The CB-2 receptor is also expressed on other immune system cells, such as lymphoid cells (S. Galiegue, et al., *Eur J Biochem*, 232, 54-61 (1995)). Agonist activation of cannabinoid receptors results in inhibition of cAMP accumulation, stimulation of MAP kinase activity, and closure of calcium channels.

There exists substantial evidence that cannabinoids regulate appetitive behavior. Stimulation of CB-1 activity by anandamide or Delta-9 THC results in increased food intake and weight gain in multiple species including humans (Williams and Kirkham, *Psychopharm.*, 143, 315-317(1999)). Genetic knock-out of CB-1 result in mice that were hypophagic and lean relative to wild-type litter mates (DiMarzo, et al., *Nature*, 410, 822-825 (2001)). Published studies with CB-1 small molecule antagonists have demonstrated decreased food intake and body weight in rats (Trillou, et. al., *Am. J. Physiol. Regul. Integr. Comp. Physiol.*, R345-R353, (2003)). Chronic administration of the CB-1 antagonist AM-251 for two weeks resulted in substantial body weight reduction and decreased adipose tissue mass (Hildebrandt, et. al., *Eur. J. Pharm*, 462, 125-132(2003)). There are multiple studies that have assessed the anorexic effect of the Sanofi CB-1 antagonist, SR-141716 (Rowland, et. al., *Pyschopharm.*, 159, 111-116 (2001); Colombo, et. al., *Life Sci.*, 63, 113-117(1998)). There are at least two CB-1 antagonists in clinical trials for regulation of appetite, Sanofi's SR-141716 and Solvay's SLV-319 Published Phase IIb data reveal that SR-141716 dose-dependently reduced body weight in human subjects over a 16 week trial period. CB-1 antagonists have also been shown to promote cessation of smoking behavior. Phase II clinical data on smoking cessation were presented in September of 2002 at Sanofi-Synthelabo's Information meeting. This data showed that 30.2% of patients treated with the highest dose of SR-141716 stayed abstinent from cigarette smoke relative to 14.8% for placebo.

DEFINITIONS

The following definitions apply to the terms as used throughout this specification, unless otherwise limited in specific instances.

As used herein, the term "alkyl" denotes branched or unbranched hydrocarbon chains containing 1 to 20 carbons, preferably 1 to 12 carbons, and more preferably 1 to 8 carbons, in the normal chain, such as, methyl, ethyl, propyl, isopropyl, butyl, sec-butyl, iso-butyl, tert-butyl, pentyl, hexyl, isohexyl, heptyl, 4,4-dimethylpentyl, octyl, 2,2,4-trimethylpentyl and the like. Further, alkyl groups, as defined herein, may optionally be substituted on any available carbon atom with one or more functional groups commonly attached to such chains, such as, but not limited to hydroxyl, halo, haloalkyl, mercapto or thio, cyano, alkylthio, cycloalkyl, heterocyclyl, aryl, heteroaryl, carboxyl, carbalkoyl, carboxamido, carbonyl, alkenyl, alkynyl, nitro, amino, alkoxy, aryloxy, arylalkyloxy, heteroaryloxy, amido, —$OPO_3H$, —$OSO_3H$, and the like to form alkyl groups such as trifluoromethyl, 3-hydroxyhexyl, 2-carboxypropyl, 2-fluoroethyl, carboxymethyl, cyanobutyl and the like.

Unless otherwise indicated, the term "cycloalkyl" as employed herein alone or as part of another group includes saturated or partially unsaturated (containing one or more double bonds) cyclic hydrocarbon groups containing 1 to 3 rings, appended or fused, including monocyclicalkyl, bicyclicalkyl and tricyclicalkyl, containing a total of 3 to 20 carbons forming the rings, preferably 3 to 10 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl,

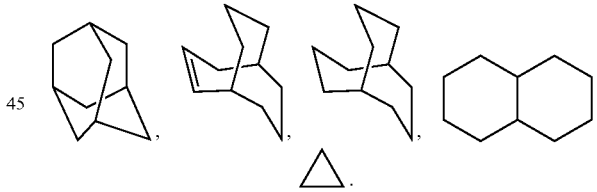

Further, any cycloalkyl may be optionally substituted through any available carbon atoms with one or more groups selected from hydrogen, halo, haloalkyl, alkyl, alkoxy, haloalkyloxy, hydroxyl, alkenyl, alkynyl, aryl, aryloxy, heteroaryl, heteroaryloxy, arylalkyl, heteroarylalkyl, alkylamido, alkanoylamino, oxo, acyl, arylcarbonylamino, amino, nitro, cyano, thiol and/or alkylthio and/or any of the alkyl substituents.

The term "cycloalkylalkyl" as used herein alone or as part of another group refers to alkyl groups as defined above having a cycloalkyl substituent, wherein said "cycloalkyl" and/or "alkyl" groups may optionally be substituted as defined above.

Unless otherwise indicated, the term "aryl" as employed herein alone or as part of another group refers to monocyclic and bicyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring, for example

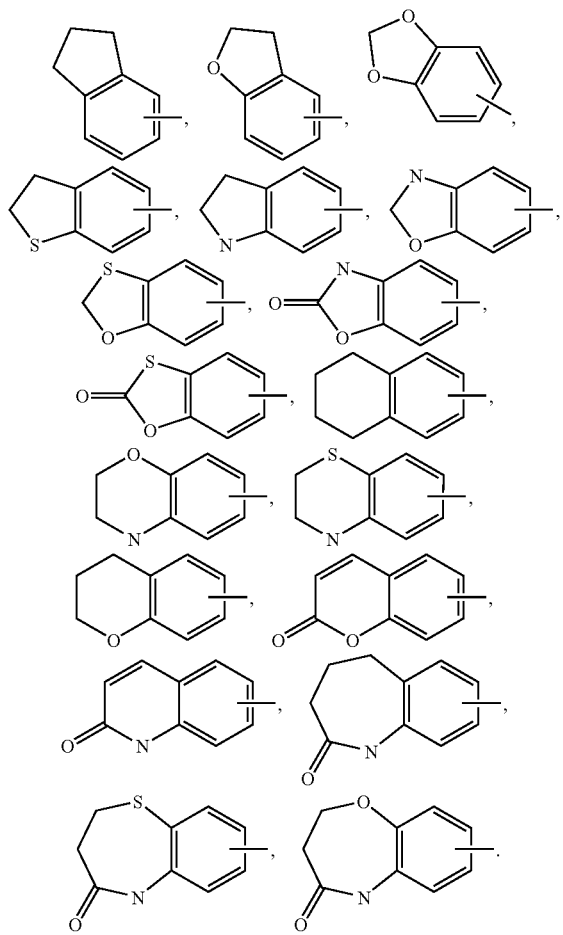

Further, "aryl", as defined herein, may optionally be substituted with one or more functional groups, such as halo, alkyl, haloalkyl, alkoxy, haloalkoxy, alkenyl, alkynyl, cycloalkyl, cycloalkylalkyl, heterocyclyl, heterocycloalkyl, aryl, heteroaryl, arylalkyl, aryloxy, aryloxyalkyl, arylalkoxy, alkoxycarbonyl, arylcarbonyl, arylalkenyl, aminocarbonylaryl, arylthio, arylsulfinyl, arylazo, heteroarylalkyl, heteroarylalkenyl, heteroarylheteroaryl, heteroaryloxy, hydroxyl, nitro, cyano, amino, substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl and/or any of the alkyl substituents set out herein.

Unless otherwise indicated, the term "heteroaryl" as used herein alone or as part of another group refers to a 5-or 6-membered aromatic ring which includes 1, 2, 3 or 4 hetero atoms such as nitrogen, oxygen or sulfur. Such rings may be fused to an aryl, cycloalkyl, heteroaryl or heterocyclyl and include possible N-oxides as described in Katritzky, A. R. and Rees, C. W., eds. *Comprehensive Heterocyclic Chemistry:* *The Structure, Reactions, Synthesis and Uses of Heterocyclic Compounds* 1984, Pergamon Press, New York, N.Y.; and Katritzky, A. R., Rees, C. W., Scriven, E. F., eds. *Comprehensive Heterocyclic Chemistry II: A Review of the Literature 1982-1995* 1996, Elsevier Science, Inc., Tarrytown, N.Y.; and references therein. Further, "heteroaryl", as defined herein, may optionally be substituted with one or more substituents such as the substituents included above in the definition of "substituted alkyl" and "substituted aryl". Examples of heteroaryl groups include the following:

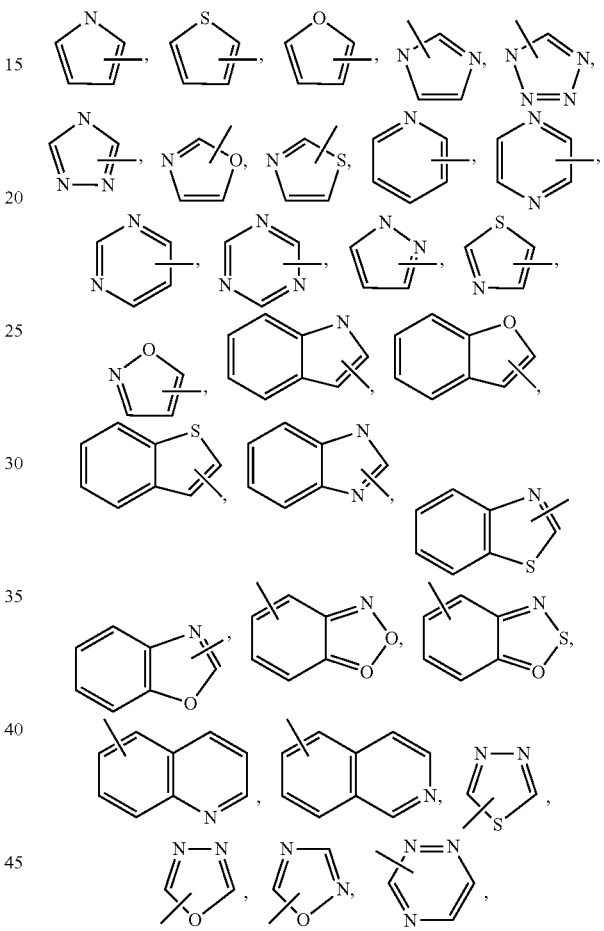

and the like.

The term "heteroarylalkyl" as used herein alone or as part of another group refers to alkyl groups as defined above having a heteroaryl substituent, wherein said heteroaryl and/or alkyl groups may optionally be substituted as defined above.

The term "heterocyclo", "heterocycle", "heterocyclyl" or "heterocyclic ring", as used herein, represents an unsubstituted or substituted stable 4 to 7-membered monocyclic ring system which may be saturated or unsaturated, and which consists of carbon atoms, with one to four heteroatoms selected from nitrogen, oxygen or sulfur, and wherein the nitrogen and sulfur heteroatoms may optionally be oxidized, and the nitrogen heteroatom may optionally be quaternized. The heterocyclic ring may be attached at any heteroatom or carbon atom which results in the creation of a stable structure. Examples of such heterocyclic groups include, but is not limited to, piperidinyl, piperazinyl, oxopiperazinyl, oxopiperidinyl, oxopyrrolidinyl, oxoazepinyl, azepinyl, pyrrolyl, pyrrolidinyl, furanyl, thienyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isooxazolyl, isoxazolidinyl, morpholinyl, thiazolyl, thiazolidinyl, isothiazolyl, thiadiazolyl, tetrahydropyranyl, thiamorpholinyl, thiamorpholinyl sulfoxide, thiamorpholinyl sulfone, oxadiazolyl and other heterocycles described in Katritzky, A. R. and Rees, C. W., eds. *Comprehensive Heterocyclic Chemistry The Structure, Reactions, Synthesis and Uses of Heterocyclic Compounds* 1984, Pergamon Press, New York, N.Y.; and Katritzky, A. R., Rees, C. W., Scriven, E. F., eds. *Comprehensive Heterocyclic Chemistry II: A Review of the Literature* 1982-1995 1996, Elsevier Science, Inc., Tarrytown, N.Y.; and references therein.

The term "heterocycloalkyl" as used herein alone or as part of another group refers to alkyl groups as defined above having a heterocyclyl substituent, wherein said heterocyclyl and/or alkyl groups may optionally be substituted as defined above.

The terms "arylalkyl", as used alone or as part of another group refer to alkyl groups as described above having an aryl substituent. Representative examples of arylalkyl include, but are not limited to, benzyl, 2-phenylethyl, 3-phenylpropyl, phenethyl, benzhydryl and naphthylmethyl and the like.

The terms "heteroarylalkyl", as used alone or as part of another group refer to alkyl groups as described above having an aryl substituent. Representative examples of heteroarylalkyl include, but are not limited to, 2-pyridinylmethyl, pyrimidinylmethyl, 4-methyl-2-pyridinylmethyl, and 2-pyridylethyl, and the like.

The term "alkoxy", "aryloxy", "heteroaryloxy" "arylalkyloxy", or "heteroarylalkyloxy" as employed herein alone or as part of another group includes an alkyl or aryl group as defined above linked through an oxygen atom. The term "halogen" or "halo" as used herein alone or as part of another group refers to chlorine, bromine, fluorine, and iodine, with bromine, chlorine or fluorine being preferred.

The term "cyano," as used herein, refers to a —CN group.

The term "methylene," as used herein, refers to a —CH$_2$— group.

The compounds of Formula I and, more particularly, Formula Ia, can be present as salts, which are also within the scope of this invention. Pharmaceutically acceptable (i.e., non-toxic, physiologically acceptable) salts are preferred. If the compounds of Formula I have, for example, at least one basic center, they can form acid addition salts. These are formed, for example, with strong inorganic acids, such as mineral acids, for example sulfuric acid, phosphoric acid or a hydrohalic acid, with organic carboxylic acids, such as alkanecarboxylic acids of 1 to 4 carbon atoms, for example acetic acid, which are unsubstituted or substituted, for example, by halogen as chloroacetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$-$C_4$) alkyl or arylsulfonic acids which are unsubstituted or substituted, for example by halogen, for example methyl-or p-toluene-sulfonic acid. Corresponding acid addition salts can also be formed having, if desired, an additionally present basic center. The compounds of Formula I and, more particularly, Formula Ia, having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono, di or tri-lower alkylamine, for example ethyl, tert-butyl, diethyl, diisopropyl, triethyl, tributyl or dimethyl-propylamine, or a mono, di or trihydroxy lower alkylamine, for example mono, di or triethanolamine. Corresponding internal salts may furthermore be formed. Salts which are unsuitable for pharmaceutical uses but which can be employed, for example, for the isolation or purification of free compounds of Formula I and, more particularly, Formula Ia, or their pharmaceutically acceptable salts, are also included.

Preferred salts of the compounds of Formula Ia which contain a basic group include monohydrochloride, hydrogensulfate, methanesulfonate, phosphate, nitrate or acetate.

Preferred salts of the compounds of Formula Ia which contain an acid group include sodium, potassium and magnesium salts and pharmaceutically acceptable organic amines.

The term "modulator" refers to a chemical compound with capacity to either enhance (e.g., "agonist" activity) or partially enhance (e.g., "partial agonist" activity) or inhibit (e.g., "antagonist" activity or "inverse agonist" activity) a functional property of biological activity or process (e.g., enzyme activity or receptor binding); such enhancement or inhibition may be contingent on the occurrence of a specific event, such as activation of a signal transduction pathway, and/or may be manifest only in particular cell types.

The term "bioactive metabolite" as employed herein refers to any functional group contained in a compound of Formula I and, more particularly, Formula Ia, with an open valence for further substitution wherein such substitution can, upon biotransformation, generate a compound of Formula I and, more particularly, Formula Ia. Examples of such functional groups of bioactive metabolites include, but are not limited to, —OH, —NH or functional groups wherein the hydrogen can be replaced with a functional group such as —PO$_3$H$_2$ for example, which, upon biotransformation generates an —OH or —NH functional group of a compound of Formula I.

The term "prodrug esters" as employed herein includes esters and carbonates formed by reacting one or more hydroxyls of compounds of Formula I and, more particularly, Formula Ia, with alkyl, alkoxy, or aryl substituted acylating agents employing procedures known to those skilled in the art to generate acetates, pivalates, methylcarbonates, benzoates and the like. Prodrug esters may also include—but are not limited to groups such as phosphate esters, phosphonate esters, phosphonamidate esters, sulfate esters, sulfonate esters, and sulfonamidate esters wherein the ester may be further substituted with groups that confer a pharmaceutical advantage such as—but not limited to—favorable aqueous solubility or in vivo exposure to the bioactive component Formula I and, more particularly, Formula Ia.

The term "prodrug" as employed herein includes functionalization of bioactive amine-or hydroxyl-containing compounds of Formula I and, more particularly, Formula Ia, to form alkyl-, acyl-, sulfonyl-, phosphoryl-, or carbohydrate-substituted derivatives. Such derivatives are formed by reacting compounds of Formula I and, more particularly, Formula Ia, with alkylating-, acylating-, sulfonylating-, or phosphorylating reagents employing procedures known to those skilled in the art. Alkylation of amines of Formula I and, more particularly, Formula Ia, may result in—but are not limited to—derivatives that include spacer units to other prodrug moieties such as substituted alkyoxymethyl-, acyloxymethyl-, phosphoryloxymethyl-, or sulfonyloxymethyl-groups. Alkylation of amines of Formula I and, more particularly, Formula Ia, may result in the generation of quaternary amine salts that act in vivo to provide the bioactive agent (i.e., the compound of Formula I, particularly Ia).

Preferred prodrugs consist of a compound of Formula Ia, where a pendant hydroxyl is phosphorylated to generate a phosphate derivative. Such a prodrug may also include a spacer group between the compound of Formula Ia, and the phosphate group, such as a methyleneoxy-group. Methods to generate such a prodrug from a compound of Formula I and, more particularly, Formula Ia, are known to those skilled in the art, and are listed in the references below.

Preferred prodrugs also consist of a compound of Formula Ia where a pendant amine, such as a pyridine group, is alkylated with a group, such as methyl, to form a quaternary ammonium ion salt. Methods to generate such a prodrug from a compound of Formula Ia are known to those skilled in the art, and are listed in the references below.

Any compound that can be converted in vivo to provide the bioactive agent (especially the compound of Formula Ia) is a prodrug within the scope and spirit of the invention.

Various forms of prodrugs are well known in the art. A comprehensive description of prodrugs and prodrug derivatives are described in:

a) *The Practice of Medicinal Chemistry*, Camille G. Wermuth et al., Ch. 31 (Academic Press, 1996);

b) *Design of Prodrugs*, edited by H. Bundgaard (Elsevier, 1985);

c) *A Textbook of Drug Design and Development*, P. Krogsgaard-Larson and H. Bundgaard, eds. Ch. 5, pp. 113-191 (Harwood Academic Publishers, 1991);

d) *Hydrolysis in Drug and Prodrug Metabolism*, B. Testa and J. M. Mayer (Verlag Helvetica Chimica Acta AG, Zurich, Switzerland; Wiley-VCH, Weinheim, Federal Republic of Germany, 2003);

e) Ettmayer, P.; Amidon, G. L.; Clement, B.; Testa, B. "Lessons Learned from Marketed and Investigational Prodrugs" *J. Med. Chem.* 2004, 47 (10), 2393-2404; and f) Davidsen, S. K. et al. "N-(Acyloxyalkyl)pyridinium Salts as Soluble Prodrugs of a Potent Platelet Activating Factor Antagonist" *J. Med. Chem.* 1994, 37 (26), 4423-4429.

Said references are incorporated herein by reference.

An administration of a therapeutic agent of the invention includes administration of a therapeutically effective amount of the agent of the invention. The term "therapeutically effective amount" as used herein refers to an amount of a therapeutic agent to treat or prevent a condition treatable by administration of a composition of the invention. That amount is the amount sufficient to exhibit a detectable therapeutic or preventative or ameliorative effect. The effect may include, for example, treatment or prevention of the conditions listed herein. The precise effective amount for a subject will depend upon the subject's size and health, the nature and extent of the condition being treated, recommendations of the treating physician, and the therapeutics or combination of therapeutics selected for administration.

DETAILED DESCRIPTION

The present application describes compounds according to Formula I, particularly and preferably Formula Ia, pharmaceutical compositions comprising at least one compound according to Formula I, particularly and preferably Formula Ia, and optionally one or more additional therapeutic agents and methods of treatment using the compounds according to Formula I particularly and preferably Formula Ia, both alone and in combination with one or more additional therapeutic agents. The compounds have the general Formula I below and particularly Formula Ia:

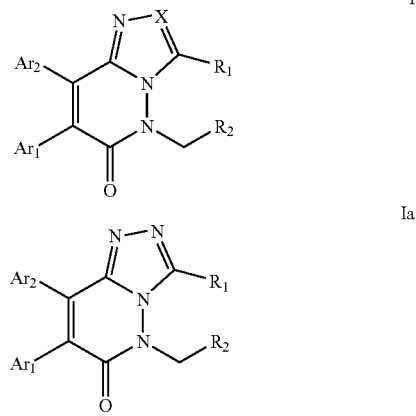

including all prodrugs, pharmaceutically acceptable salts and stereoisomers (particularly pharmaceutically acceptable salts), wherein:

$Ar_1$ is aryl (particularly phenyl), which may be optionally substituted with 1-3 members selected from the group consisting of halogen (particularly chloro and fluoro), haloalkyl (particularly trifluoromethyl) cyano, alkyl (particularly methyl and ethyl), alkoxy (particularly methoxy), and haloalkoxy (particularly trifluoromethoxy and difluoromethoxy);

$Ar_2$ is aryl (particularly phenyl), which may be optionally substituted with 1-3 members selected from the group consisting of halogen (particularly chloro and fluoro), haloalkyl (particularly trifluoromethyl), cyano, alkyl (particularly methyl and ethyl), alkoxy (particularly methoxy), and haloalkoxy (particularly trifluoromethoxy and difluoromethoxy);

X is N to give compounds of Formula Ia which is shown above;

$R_1$ is alkyl (particularly methyl, ethyl and isopropyl), wherein the alkyl group is substituted with either an —$OR_4$ or an —$NR_5R_6$ group;

$R_2$ is selected from the group consisting of aryl (particularly phenyl) and heteroaryl (particularly 2-pyridyl and 3-pyridyl), wherein the aryl and heteroaryl may each be optionally substituted with 1-2 members selected from the group consisting of halogen (particularly fluoro and chloro), alkyl (particularly methyl, ethyl, propyl and isopropyl), haloalkyl (particularly trifluoromethyl and difluoromethyl), cyano, cycloalkyl (particularly cyclopropyl and cylobutyl), and alkoxy (particularly methoxy and ethoxy);

$R_4$ is selected from the group consisting of hydrogen, alkyl (particularly methyl and ethyl), haloalkyl (particularly trifluoromethyl, and difluoromethyl), and phosphates (particularly —$PO_3Na_2$ and —$PO_3HNa$);

$R_5$ and $R_6$ are each independently selected from the group consisting of hydrogen and alkyl (particularly methyl and ethyl), wherein the alkyl may be optionally substituted with 1-3 halogen (particularly fluoro); or $R_5$ and $R_6$ may be taken together with the nitrogen to which they are attached to form a heterocyclyl ring forming a 4, 5, 6, or 7 membered rings.

In a first particular embodiment, compounds of the present invention are provided in which:

$R_1$ is a methyl, ethyl or isopropyl group which is substituted with an —$OR_4$ or —$NR_5R_6$ group;

$R_4$ is selected from the group consisting of hydrogen, methyl, ethyl, isopropyl, and phosphate;

$R_5$ and $R_6$ are each independently selected from the group consisting of hydrogen, methyl, ethyl, propyl and isopropyl; or $R_5$ and $R_6$ are together with the nitrogen to which they are attached to form a 4, 5, 6, or 7-membered ring having 1 nitrogen and the remainder of the ring members as carbon.

In a second embodiment, compounds of the present invention are provided in which:

$R_2$ is selected from the group consisting of heteroaryl (particularly 2-pyridinyl, and 3-pyridinyl), which may be optionally substituted with 1-3 members selected from the group consisting of chloro, fluoro, methyl, ethyl, isopropyl, cyclopropyl, cyclobutyl, trifluoromethyl, cyano, and hydroxymethyl; in particular, the heteroaryl is a pyridinyl group;

In a third embodiment, compounds of the present invention are provided in which:

$Ar_1$ is selected from the group consisting of phenyl optionally substituted with methyl, trifluoromethyl, chloro, fluoro or cyano (with particular examples of $Ar_1$ being phenyl and particular examples of $Ar_1$ when substituted being 4-methylphenyl, 4-trifluoromethylphenyl, 4-chlorophenyl, 4-cyanophenyl, and 4-fluorophenyl);

$Ar_2$ is selected from the group consisting of phenyl optionally substituted with methyl, methoxy, trifluoromethyl, chloro, fluoro or cyano (with particular examples of $Ar_2$ being phenyl and particular examples of $Ar_2$ when substituted being 4-chlorophenyl, 4-cyanophenyl, 4-fluorophenyl, 4-methylphenyl, 4-trifluoromethylphenyl and 4-methoxyphenyl);

$R_1$ is selected from the group consisting of —$CH_2OR_4$, —$CH(CH_3)OR_4$, —$C(CH_3)_2OR_4$, —$CH_2CH_2OR_4$, —$CH_2NR_5R_6$, —$CH(CH_3)NR_5R_6$ and —$C(CH_3)_2NR_5R_6$;

$R_2$ is selected from the group consisting of aryl (particularly phenyl) and heteroaryl (particularly 2-pyridyl and 3-pyridyl), wherein the aryl and heteroaryl may each be optionally substituted with 1-2 members selected from the group consisting of halogen (particularly fluoro and chloro), alkyl (particularly methyl, ethyl, propyl and isopropyl), haloalkyl (particularly trifluoromethyl and difluoromethyl), cyano, cycloalkyl (particularly cyclopropyl and cyclobutyl), and alkoxy (particularly methoxy and ethoxy);

$R_4$ is selected from the group consisting of hydrogen, methyl ethyl, and —$P(O)(OH)_2$;

$R_5$ and $R_6$ are each independently selected from the group consisting of hydrogen and methyl.

In a fourth embodiment $R_2$ is selected from the group consisting of (a) phenyl substituted with cyano (to give, for example, 4-cyanophenyl);

(b) pyridyl substituted with 1-2 members selected from the group consisting of methyl, ethyl, isopropyl, and trifluoromethyl (for example, to give a substituted pyridyl selected from the group consisting of 4-trifluoromethyl-2-pyridyl, 4-trifluoromethyl-3-pyridyl, 2-methyl-4-trifluoromethyl-3-pyridyl, 2-ethyl-4-trifluoromethyl-3-pyridyl, and 2-isopropyl-4-trifluoromethyl-3-pyridyl).

In a fifth embodiment, compounds of the present invention are provided in which $R_4$ is —$P(O)(OH)(ONa)$ or —$P(O)(ONa)_2$.

In still yet another embodiments, pharmaceutical compositions are provided which comprise one or more compounds of the present invention alone or in combination with a pharmaceutically acceptable carrier and/or at least one additional therapeutic agent, for example, an anti-obesity agent; an appetite suppressant; an anti-diabetic agent; an anti-hyperlipidemia agent; a hypolipidemic agent; a hypocholesterolemic agent; a lipid-modulating agent; a cholesterol-lowering agent; a lipid-lowering agent; an HDL-raising agent, an anti-hypertensive agent; an agent used to treat a sleep disorder; an agent used to treat substance abuse and/or an addictive disorder; an anti-anxiety agent; an anti-depressant; an anti-psychotic agent; a cognition enhancing agent; an agent used to treat a cognitive disorder; an agent used to treat Alzheimer's disease; an agent used to treat Parkinson's disease; an anti-inflammatory agent; an agent used to treat neurodegeneration; an agent used to treat arteriosclerosis; an agent used to treat a respiratory condition; an agent used to treat a bowel disorder; a cardiac glycoside; and an anti-tumor agent, are provided.

In one particular embodiment, methods for treating, preventing or slowing the progression of obesity in a patient (including a human being either male or female) by administering to a patient in need of such treatment an obesity treating, preventing or slowing amount of a compound and/or pharmaceutical composition of the present invention are provided.

In another particular embodiment, methods for smoking cessation in a patient (including a human being either male or female) by administering to a patient in need a smoking cessation amount of a compound and/or pharmaceutical composition of the present invention are provided.

In one embodiment, compounds of the present invention provide a class of new azabicyclic heterocyclic compounds having an unexpectedly desirable combination of effective CB-1 inverse agonist activity and aqueous solubility or canine half-life as compared to known modulators of CB-1 inverse agonist activity.

For example, the triazolopyridazines described in U.S. application Ser. No. 11/454,324, filed on Jun. 16, 2006 and published on Dec. 21, 2006 (WO2006/138682, published on Dec. 28, 2006), and assigned to Bristol-Myers Squibb Company, have CB-1 Ki values of 2 nM-1000 nM but with long canine half-life values of >100 hrs according to the assay(s) described, infra. And solubility of <1 μg/mL. In contrast, compounds of the present invention demonstrate unexpected combination of high CB-1 inverse agonist activity and a short canine half-life or have increased aqueous solubility. The compounds of the instant invention have CB-1 Ki values of 0.5 nM-20 nM with and canine half-life values of <50 hr or have increased aqueous solubility of >1 μg/mL.

All stereoisomers of the compounds of the instant invention are contemplated, either in mixture or in pure or substantially pure form. The compounds of the present invention can have asymmetric centers at any of the carbon atoms including any one of the R substituents. Consequently, compounds of Formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic techniques, chiral HPLC or fractional crystallization.

It will be understood that any given exemplary embodiment can be combined with one or more additional exemplary embodiments.

The compounds of Formula I of the invention can be prepared as shown in the following reaction schemes and description thereof, as well as relevant published literature procedures that may be used by one skilled in the art. Exemplary reagents and procedures for these reactions appear hereinafter and in the working Examples.

The following abbreviations are employed in the Schemes, Examples and elsewhere herein:
Ac=acetyl
AcOH=acetic acid
Boc=tert-butoxycarbonyl
DCM=dichloromethane
DIPEA=N,N-diisopropylethylamine
DMF=N,N-dimethylformamide
EDAC=1-(3-Dimethylaminopropyl)-3-ethylcarbodiimide hydrochloride
EtOAc=ethyl acetate
$Et_3N$=triethylamine
$Et_2O$=diethyl ether
HEX=hexanes
HOBt=1-hydroxybenzotriazole hydrate
HPLC=high performance liquid chromatography
LAH=lithium aluminum hydride
LCMS=liquid chromatography mass spectrometry
MeOH=methanol
MS or Mass Spec=mass spectrometry
NaOH=sodium hydroxide
PG=protecting group
rt=room temperature
TFA=trifluoroacetic acid
THF=tetrahydrofuran
min=minute(s)
hr(s)=hour(s)
L=liter
mL or ml=milliliter
µL=microliter
g=gram(s)
mg=milligram(s)
mol=moles
mmol=millimole(s)
nM=nanomolar Compounds of the present invention may be prepared by procedures illustrated in the accompanying schemes.

Methods of Preparation

The compounds of the present invention may be prepared by methods such as those illustrated in the following Scheme 1 and 2 and as described below in the preparation of the Example compounds. Solvents, temperatures, pressures, and other reaction conditions may readily be selected by one of ordinary skill in the art. Starting materials are commercially available or can be readily prepared by one of ordinary skill in the art using known methods. For all of the schemes and compounds described below, $R_1$, $R_2$, $R_4$, $R_5$, $R_6$, $Ar_1$, and $Ar_2$ are as described for a compound of Formula Ia.

Scheme 1

Compounds of formula i and of formula ii are commercially available or can readily be prepared by literature methods. Compounds of formula i are condensed with compounds of formula ii using basic conditions, such as the use of a potassium or sodium alkyloxide (for example potassium t-butoxide), in an inert solvent (such as DMF) to give compounds of formula iii. Compounds of formula iii are reacted with bis-Boc-hydrazine under basic conditions using a base such as DBU. The resulting product is the treated with an acid (such as HCl) to give compounds of formula iv. Compounds of formula v are prepared from compounds of formula iv by reacting compounds of formula iv with an electrophilic bromine source (such as $Br_2$) under basic conditions. Compounds of formula vi are prepared from compounds of formula v by treating compounds of formula v with a base (such as LiOH or $K_2CO_3$) and an alkylating or benzylating agent (such as an alkyl-bromide, aryl-alkyl-bromide) or an heteroaryl-alkyl bromide. Compounds of formula vi are then reacted as described in Scheme 2 and 3.

Scheme 2

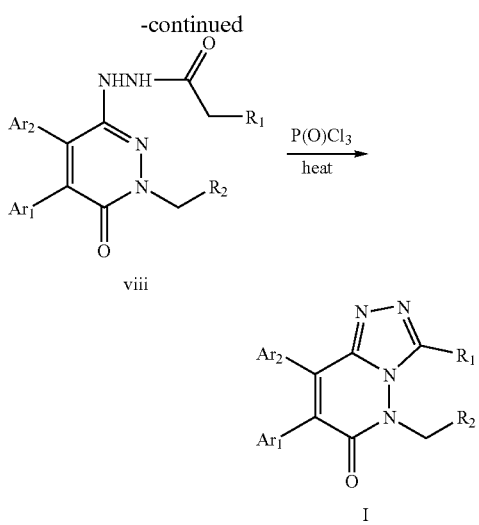

Scheme 2 describes the preparation of compounds of Formula Ia. Compounds of formula vii are prepared from compounds of formula vi by treating compounds of formula vi with hydrazine in pyridine at an elevated temperature (for example, in the range of 100 to 250 °C.) optionally under microwave assisted conditions; or by using a Suzuki reaction (well known to chemists) with Boc-hydrazine followed by removal of the Boc group using acidic conditions such as TFA. Compounds of formula viii are prepared from compounds of formula vii by reacting compounds of formula vii with an acyl-chloride in the presence of a tertiary amine base, such as triethylamine. Compounds of formula viii are then cyclized using $P(O)Cl_3$ to give compounds of Formula Ia.

Parallel synthesis may be employed in the preparation of compounds, for example, where the intermediates possess an activated reaction center such as, but not limited to, (a) a reactive heteroaryl chloride for Suzuki coupling chemistry or (b) a carboxylic acid for amide coupling chemistry or (c) a reactive halide for alkylation chemistry or (d) an activated chloride for displacement chemistry by for example an alcohol.

EXAMPLES

The following Examples are offered as illustrative as a partial scope of the invention, including preferred embodiments, but are not meant to be limiting of the scope of the invention. Unless otherwise indicated, they have been prepared, isolated and characterized using the methods disclosed herein. The abbreviations used herein are defined above. The analytical HPLC/MS methods and NMR methods used are as described herein.

Analytical HPLC Methods Employed in Characterization of Examples

Analytical HPLC/MS was performed on Shimadzu LC10 AS liquid chromatography systems and Waters ZMD Mass Spectrometers using the following methods:

Method A. Linear gradient of 0 to 100% solvent B over 4 min, with 1 min hold at 100% B;
UV visualization at 220 nm
Column: YMC S5 ODS COMBISCREEN C18, 4.6×50 mm
Flow rate: 4 ml/min
Solvent A: 0.2% phosphoric acid, 90% water, 10% methanol
Solvent B: 0.2% phosphoric acid, 90% methanol, 10% water Method B. Linear gradient of 0 to 100% solvent B over 4 min, with 1 min hold at 100% B;
UV visualization at 220 nm
Column: PHENOMENEX LUNA C18, 4.6×50 mm
Flow rate: 4 ml/min
Solvent A: 0.1% trifluoroacetic acid, 90% water, 10% methanol
Solvent B: 0.1% trifluoroacetic acid, 90% methanol, 10% water Method C. Linear gradient of 40% to 95% solvent B over 15 min
UV visualization at 220 nm
Column: PHENOMENEX LUNA Phenyl-hexyl 4.6×150 mm
Flow rate: 1.2 ml/min
Solvent A: 0.1% ammonium acetate, 100% water
Solvent B: 0.1% ammonium acetate, 100% Acetonitrile NMR Employed in Characterization of Examples $^1$H NMR spectra were obtained with Bruker or JOEL fourier transform spectrometers operating at the following frequencies: $^1$H NMR: 400 MHz (Bruker), 400 MHz (JOEL), or 500 MHz (JOEL); $^{13}$C NMR: 100 MHz (Bruker), 100 MHz (JOEL) or 125 MHz (JOEL). Spectra data are reported as Chemical shift (multiplicity, number of hydrogens, coupling constants in Hz) and are reported in ppm($\delta$ units) relative to either an internal standard (tetramethylsilane =0 ppm) for $^1$H NMR spectra, or are referenced to the residual solvent peak (2.49 ppm for $CD_2HSOCD_3$, 3.30 ppm for $CD_2HOD$, 7.24 ppm for $CHCl_3$, 39.7 ppm for $CD_3SOCD_3$, 49.0 ppm for $CD_3OD$, 77.0 ppm for $CDCl_3$). All $^{13}$C NMR spectra were proton decoupled.

Example 1

Preparation of 4-(6-bromo-5-(4-chlorophenyl)-3-oxo-2,3-dihydropyridazin-4-yl)benzonitrile

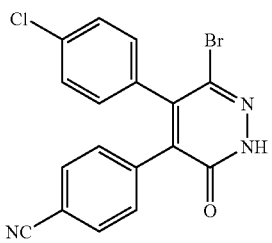

Example 1A 4-(4-(4-chlorophenyl)-2-oxo-2,5-dihydrofuran-3-yl)benzonitrile

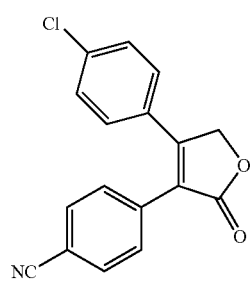

To a stirred and cooled (−15° to −10° C.) solution of 2-(4-cyanophenyl)acetic acid (35 g, 217.18 mmol) in DMF (250 mL) was added potassium t-butoxide (95%, 25.66 g, 217.22 mmol) under argon in small portions keeping the temperature below −10° C. After the addition was complete a solution of 2-bromo-1-(4-chlorophenyl)ethanone (50.71 g, 217.18 mmol) in DMF (75 mL) was added slowly over 30 min. The reaction mixture was stirred for 1 hr keeping the temperature between −10° to 0° C. Et₃N (12.0 mL, 86.1 mmol) was added at 0° C. and the reaction mixture was allowed to warm to room temperature over 1.5 hr. Then EtOH (70 mL) was added at room temperature and the reaction mixture was stirred for 10 min. The reaction mixture was cooled in an ice bath and water (300 mL) was added slowly. The light green precipitate formed was collected by filtration, washed thoroughly with water followed by hexanes. The solid thus obtained was dried in a vacuum oven overnight at 50° C. to obtain 4-(4-(4-chlorophenyl)-2-oxo-2,5-dihydrofuran-3-yl)benzonitrile (58.2 g, 91% yield) as a light green solid.

Example 1B 4-(5-(4-chlorophenyl)-3-oxo-2,3-dihydropyridazin-4-yl)benzonitrile

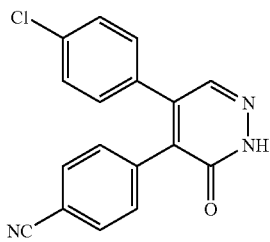

To a stirred solution of 4-(4-(4-chlorophenyl)-2-oxo-2,5-dihydrofuran-3-yl)benzonitrile (58.2 g, 196.81 mmol) in CH₂Cl₂ (300 mL) was added DBU (1.55 mL, 10.36 mmol) at room temperature under argon followed by the slow addition of a solution of di-tert-butyl azo-dicarboxylate (98%, 46.24 g, 196.8 mmol) in CH₂Cl₂ (100 mL) over 20 min. The reaction mixture was stirred at room temperature for 20 min. After this time, CH₃CN (200 mL) was added to the reaction mixture followed by the addition of 4.0 M solution of HCl in dioxane (200 mL) at room temperature. The reaction mixture was stirred at 60° C. for 2.5 hr and a thick precipitate formed as the reaction proceeded. The reaction mixture was cooled to room temperature and diluted with CH₃CN (200 mL). The solid was collected by filtration, washed with CH₃CN (2×100 mL) and air dried to obtain a tan solid which was used directly in the next step. To the tan solid in MeOH (440 mL) at room temperature under argon was added NaOAc (64.6 g, 787.5 mmol). The reaction mixture was stirred at 65° C. for 2.5 hr. The reaction mixture was cooled to room temperature and concentrated under reduced pressure to remove most of the MeOH. Water (440 mL) was added and the resulting suspension was stirred at room temperature for 10 min. The solid was filtered, washed thoroughly with water followed by hexanes and dried in a vacuum oven at 50° C. overnight to furnish 4-(5-(4-chlorophenyl)-3-oxo-2,3-dihydropyridazin-4-yl)benzonitrile (44.9 g, 74% yield) as a light yellow solid.

Example 1C

Preparation of 4-(6-bromo-5-(4-chlorophenyl)-3-oxo-2,3-dihydropyridazin-4-yl)benzonitrile

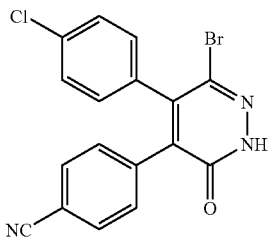

To a stirred solution of 4-(5-(4-chlorophenyl)-3-oxo-2,3-dihydropyridazin-4-yl)benzonitrile (10 g, 32.5 mmol) and LiOH.H₂O (1.37 g, 32.65 mmol) in MeOH (200 mL) at 70° C. was added bromine (2.6 g, 16.26 mmol). The reaction mixture was stirred at 70° C. for 3 min. After this time, bromine (5.2 g, 32.5 mmol) and LiOH.H₂O (2.74 g, 65.3 mmol) were added and the reaction mixture was stirred at 70° C. for an additional 3 min. After this time, another portion of bromine (2.6 g, 16.26 mmol) and LiOH.H₂O (1.37 g, 32.65 mmol) was added and the reaction mixture was stirred for 3 min at 70° C. A final portion of bromine (2.6 g, 16.26 mmol) followed by LiOH.H₂O (1.37 g, 32.65 mmol) was added and the reaction mixture was stirred at 70° C. for another 3 min. HPLC (Method A) showed disappearance of the starting material. The reaction mixture was cooled to room temperature and concentrated under reduced pressure to give a light yellow solid. This solid was diluted with water (100 mL) and the pH was adjusted to 7 with aq 1.0 N NaOH. The product was extracted with EtOAc (2×100 mL). The combined organic layer was washed with saturated NaCl, dried (MgSO₄), filtered and the filtrate was concentrated to obtain 4-(6-bromo-5-(4-chlorophenyl)-3-oxo-2,3-dihydropyridazin-4-yl)benzonitrile as a pale yellow solid (12.1 g, 96%).

Example 2

Preparation of 4-(8-(4-chlorophenyl)-3-(methoxymethyl)-5-((2-methyl-6-(trifluoromethyl)pyridin-3-yl)methyl)-6-oxo-5,6-dihydro-[1,2,4]triazolo[4,3-b]pyridazin-7-yl)benzonitrile

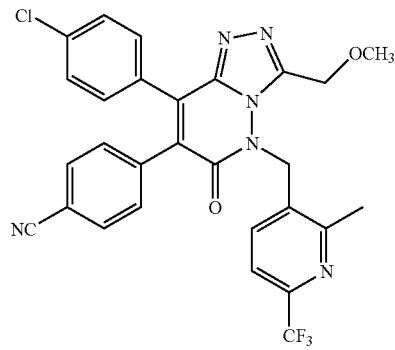

Example 2A 4-(6-bromo-5-(4-chlorophenyl)-2-((2-methyl-6-(trifluoromethyl)pyridin-3-yl)methyl)-3-oxo-2,3-dihydropyridazin-4-yl)benzonitrile

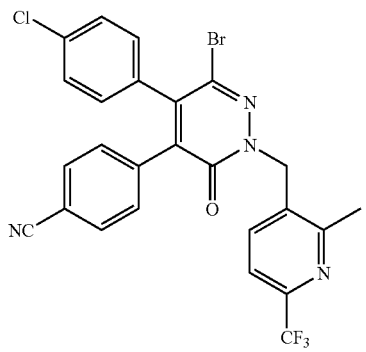

To 4-(5-(4-chlorophenyl)-3-oxo-2,3-dihydropyridazin-4-yl)benzonitrile (7.2 mmol) in 20 mL DMF was added LiOH monohydrate (0.612 g, 14.40 mmol) and 3-(chloromethyl)-2-methyl-6-(trifluoromethyl)pyridine (1.65 g, 7.91 mmol) at room temperature under Ar. The reaction mixture was heated to 70° C. and stirred for 1 hr. After this time, water (50 ml) and EtOAc (50 ml) were added to the reaction mixture and the resulting solution was stirred for 10 minutes. The layers were separated and the organic phase was washed with saturated NaCl (100 mL). The organic layer was dried (Na$_2$SO$_4$), filtered and concentrated. The residue was purified using an ISCO automated column chromatography system (120 g silica gel, 20%-80% EtOAc/Hex) to give the product as an off-white solid (3.27 g, 81% yield). HPLC retention time 3.91 min (Method A); LCMS (M+H)=561.0.

Example 2B 4-(5-(4-chlorophenyl)-6-hydrazinyl-2-((2-methyl-6-(trifluoromethyl)pyridin-3-yl)methyl)-3-oxo-2,3-dihydropyridazin-4-yl)benzonitrile

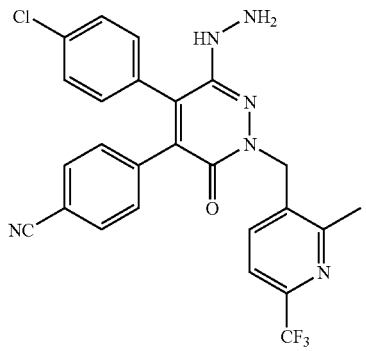

To a microwave flask was added 4-(6-bromo-5-(4-chlorophenyl)-2-((2-methyl-6-(trifluoromethyl)pyridin-3-yl)methyl)-3-oxo-2,3-dihydropyridazin-4-yl)benzonitrile (105 mg, 0.187 mmol), pyridine (10 ml) and anhydrous hydrazine (60 mg, 1.87 mmol). The reaction was subjected to microwave at 200° C. for 30 min. After this time the solvent was removed to give 4-(5-(4-chlorophenyl)-6-hydrazinyl-2-((2-methyl-6-(trifluoromethyl)pyridin-3-yl)methyl)-3-oxo-2,3-dihydropyridazin-4-yl)benzonitrile as a yellow solid. The material was used in the next step without further purification.

Example 2C

N'-(4-(4-chlorophenyl)-5-(4-cyanophenyl)-1-((2-methyl-6-(trifluoromethyl)pyridin-3-yl)methyl)-6-oxo-1,6-dihydropyridazin-3-yl) -2-methoxyacetohydrazide

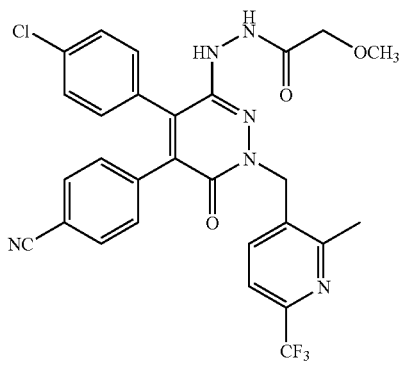

To a solution of 4-(5-(4-chlorophenyl)-6-hydrazinyl-2-((2-methyl-6-(trifluoromethyl)pyridin-3-yl)methyl)-3-oxo-2,3-dihydropyridazin-4-yl)benzonitrile (1200 mg, 2.344 mmol) in THF (15 ml) was added Et$_3$N (471 mg, 4.668 mmol) followed by 2-methoxyacetyl chloride (254 mg, 2.344 mmol). The reaction was stirred at room temperature for 20 min. After this time, the reaction was diluted with EtOAc (100 ml) and the resulting solution was wash with water (2×50 ml) and saturated NaCl (50 ml). The organic layer was dried (MgSO$_4$), filtered and concentrated. The residue was purified using an ISCO automated chromatography system (120 g silica gel, 20-60% EtOAc/CH$_2$Cl$_2$) to the give product N'-(4-(4-chlorophenyl)-5-(4-cyanophenyl)-1-((2-methyl-6-(trifluoromethyl)pyridin-3-yl)methyl)-6-oxo-1,6-dihydropyridazin-3-yl)-2-methoxyacetohydrazide as a light yellow solid 780 mg (57% yield). HPLC retention time 2.858 min (Method A); LCMS (M+H)=583.0.

Example 2D 4-(8-(4-chlorophenyl)-3-(methoxymethyl)-5-((2-methyl-6-(trifluoromethyl)pyridin-3-yl)methyl)-6-oxo-5,6-dihydro-[1,2,4]triazolo[4,3-b]pyridazin-7-yl)benzonitrile

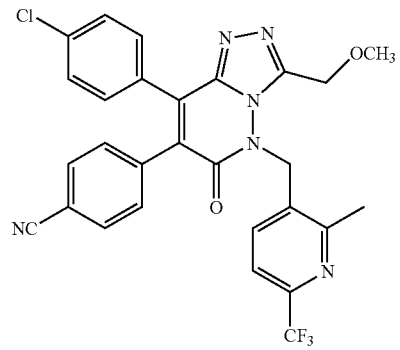

N'-(4-(4-chlorophenyl)-5-(4-cyanophenyl)-1-((2-methyl-6-(trifluoromethyl)pyridin-3-yl)methyl)-6-oxo-1,6-dihydropyridazin-3-yl) -2-methoxyacetohydrazide (780 mg, 1.338 mmol) was dissolved in toluene (25 ml) and was heated at 120° C. for 15 min. After this time, POCl₃ (5 ml) was added and the reaction was stirred at 120° C. for an additional 2 hr. The reaction mixture was then cooled to room temperature and concentrated under reduced pressure. The resulting residue was dissolved in EtOAc (50 ml) and washed with saturated NaHCO₃ (20 ml), water (20 ml) and saturated NaCl (20 ml). The organic layer was dried (MgSO₄), filtered and concentrated. The residue was purified using an ISCO automated system (80 g silica gel, 20%-80% EtOAc/Hex) to give the product 4-(8-(4-chlorophenyl)-3-(methoxymethyl)-5-((2-methyl-6-(trifluoromethyl)pyridin-3-yl)methyl)-6-oxo-5,6-dihydro-[1,2,4]triazolo[4,3-b]pyridazin-7-yl)benzonitrile (550 mg) as an off-white solid (73% yield). HPLC retention time 3.085 min (Method A); LCMS (M+H)=565.0. ¹HNMR (CD₃CN, 500 Hz) 7.67(1H, d, J=7.7Hz), 7.63(2H, d, J=8.8 Hz), 7.58(1H, d, J=7.75), 7.35-7.37(6H, m), 5.81(2H, s), 4.40(2H, s), 3.24(3H, s), 2.65(3H, s); ¹³CNMR (CD₃CN, 500 Hz) 160.24, 157.25, 146.50(m), 146.00, 144.71, 139.15, 137.77, 135.93, 134.84, 134.25, 132.92, 132.64, 131.38, 129.26, 122.90(m), 119.25, 112.66, 65.06, 58.28, 50.01, 22.19.

Example 3

Preparation of 4-(8-(4-chlorophenyl)-3-(hydroxymethyl)-5-((2-methyl-6-(trifluoromethyl)pyridin-3-yl)methyl)-6-oxo-5,6-dihydro-[1,2,4]triazolo[4,3-b]pyridazin-7-yl)benzonitrile

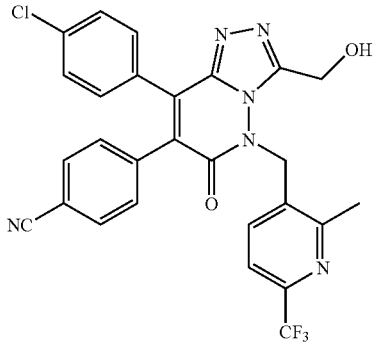

Example 3A 2-chloro-N'-(4-(4-chlorophenyl)-5-(4-cyanophenyl)-1-((2-methyl-6-(trifluoromethyl)pyridin-3-yl)methyl)-6-oxo-1,6-dihydropyridazin-3-yl)acetohydrazide

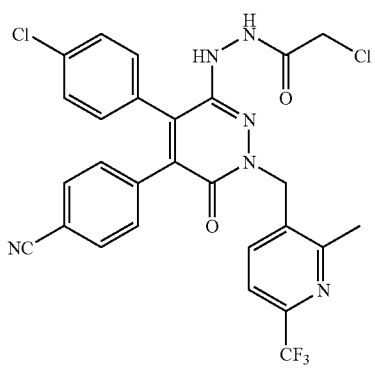

To a solution of 4-(5-(4-chlorophenyl)-6-hydrazinyl-2-((2-methyl-6-(trifluoromethyl)pyridin-3-yl)methyl)-3-oxo-2,3-dihydropyridazin-4-yl)benzonitrile (500 mg, 0.977 mmol) in THF (7 ml), Et₃N (197 mg, 1.953 mmol) was added chloroacetyl chloride (110 mg, 0.977 mmol). The reaction was stirred at room temperature for 30 min. The reaction mixture was diluted with EtOAc (50 ml) and the resulting solution was washed with water (2×20 ml) and saturated NaCl (20 ml). The organic layer was dried (MgSO₄), filtered and concentrated. The residue was purified using an ISCO automated chromatography system (12 g silica gel, 20-40% EtOAc/CH₂Cl₂) to give the product 2-chloro-N'-(4-(4-chlorophenyl)-5-(4-cyanophenyl)-1-((2-methyl-6-(trifluoromethyl)pyridin-3-yl)methyl)-6-oxo-1,6-dihydropyridazin-3-yl)acetohydrazide as a light yellow solid (410 mg, 72% yield). HPLC retention time 2.920 min (Method A); LCMS (M+H)=587.0.

Example 3B 4-(3-(chloromethyl)-8-(4-chlorophenyl)-5-((2-methyl-6-(trifluoromethyl)pyridin-3-yl)methyl)-6-oxo-5,6-dihydro-[1,2,4]triazolo[4,3-b]pyridazin-7-yl)benzonitrile

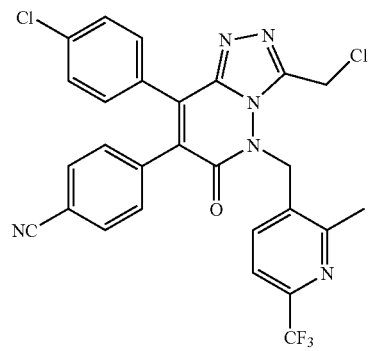

To a round bottom flask was added 2-chloro-N'-(4-(4-chlorophenyl)-5-(4-cyanophenyl)-1-((2-methyl-6-(trifluoromethyl)pyridin-3-yl)methyl)-6-oxo-1,6-dihydropyridazin-3-yl)acetohydrazide (400 mg, 0.681 mmol) and toluene (10 ml). The mixture was heated at 120° C. for 5 min. After this time, POCl₃ (1.5 ml) was added and the reaction was stirred at 120° C. for an additional 6 hr. The reaction mixture was then cooled to room temperature and concentrated to dryness under reduced pressure. The resulting residue was dissolved in EtOAc (50 ml) and washed with saturated NaHCO₃ (20 ml), water (20 ml), and saturated NaCl (20 ml). The organic layer was dried (MgSO₄), filtered and concentrated. The residue was purified using an ISCO automated chromatography system (12 g silica gel, 20%-40% EtOAc/Hex) to give the product 4-(3-(chloromethyl)-8-(4-chlorophenyl)-5-((2-methyl-6-(trifluoromethyl)pyridin-3-yl)methyl)-6-oxo-5,6-dihydro-[1,2,4]triazolo[4,3-b]pyridazin-7-yl)benzonitrile (210 mg) as an off-white solid (54% yield). HPLC retention time 3.148 min (Method A); LCMS (M+1)=569.0.

Example 3C 4-(8-(4-chlorophenyl)-3-(hydroxymethyl)-5-((2-methyl-6-(trifluoromethyl)pyridin-3-yl)methyl)-6-oxo-5,6-dihydro-[1,2,4]triazolo[4,3-b]pyridazin-7-yl)benzonitrile

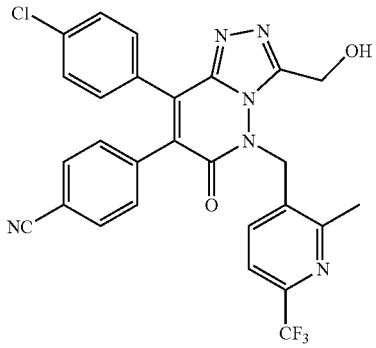

To a round bottom flask was added 4-(3-(chloromethyl)-8-(4-chlorophenyl)-5-((2-methyl-6-(trifluoromethyl)pyridin-3-yl)methyl)-6-oxo-5,6-dihydro-[1,2,4]triazolo[4,3-b]pyridazin-7-yl)benzonitrile (30 mg, 0.053 mmol), sodium iodide (40 mg, 0.264 mmol) and acetone (2 ml). The reaction was stirred at room temperature for 8 hr. After this time, water (0.3 ml) was added followed by 1 drop of 1N NaOH. The reaction was stirred at room temperature for an additional 14 hrs. The solution was then diluted with EtOAc (25 ml) and washed with water (2×15 ml) and saturated NaCl (15 ml). The organic layer was dried (MgSO$_4$), filtered and concentrated. The crude material was purified using an ISCO automated chromatography system (4 g silica gel, 20%-50% EtOAC/CH$_2$Cl$_2$) to give the product 4-(8-(4-chlorophenyl)-3-(hydroxymethyl)-5-((2-methyl-6-(trifluoromethyl)pyridin-3-yl)methyl)-6-oxo-5,6-dihydro-[1,2,4]triazolo[4,3-b]pyridazin-7-yl)benzonitrile as a white solid (15 mg, 51% yield). HPLC retention time 2.990 min (Method A); LCMS (M+1)=551.0. $^1$HNMR (CDCl$_3$, 500 Hz) 7.61(2H, d, J=8.25 Hz), 7.52(1H, d, J=7.7 Hz), 7.30-7.37(7H, m), 6.05(2H, s), 4.60(2H, s), 2.78(3H, s); $^{13}$CNMR (CDCl$_3$, 500 Hz) 161.00, 158.90, 156.25, 146.20, 144.10, 137.10, 136.80, 132.80, 131.96, 131.74, 129.90, 129.09, 118.00, (m), 113.00, 100.00, 55.10, 49.10, 22.10.

Example 4

Preparation of (R)-4-(8-(4-chlorophenyl)-3-(1-hydroxyethyl)-5-((2-methyl-6-(trifluoromethyl)pyridin-3-yl)methyl)-6-oxo-5,6-dihydro-[1,2,4]triazolo[4,3-b]pyridazin-7-yl)benzonitrile

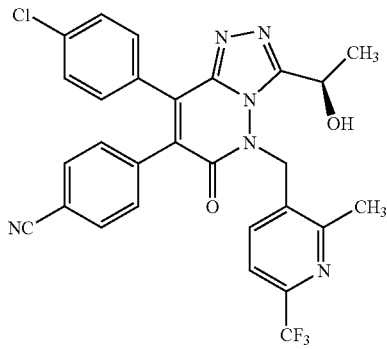

Example 4A (R)-2-(benzyloxy)-N'-(4-(4-chlorophenyl)-5-(4-cyanophenyl)-1-((2-methyl-6-(trifluoromethyl)pyridin-3-yl)methyl)-6-oxo-1,6-dihydropyridazin-3-yl)propanehydrazide

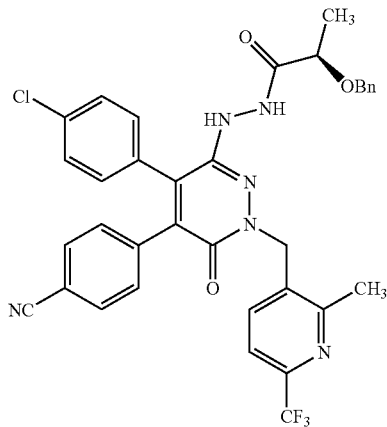

To a round bottom flask was added 4-(5-(4-chlorophenyl)-6-hydrazinyl-2-((2-methyl-6-(trifluoromethyl)pyridin-3-yl)methyl)-3-oxo-2,3-dihydropyridazin-4-yl)benzonitrile (70 mg, 0.1367 mmol), prepared as described in Example 2B, (R)-2-(benzyloxy)propanoic acid (25 mg, 0.1367 mmol), EDAC (30 mg, 0.150 mmol), HOBT (20.3 mg, 0.150 mmol), THF (5 ml) and diisopropylethyl amine (19.4 mg, 0.150 mmol). The reaction was stirred at rt for 5 hr. The reaction was diluted with EtOAc (40 ml). The resulting organic solution was extracted with water (2×20 ml) and saturated NaCl (20 ml). The organic layer was dried over MgSO$_4$, filtered and concentrated. The resulting residue was purified by silica gel column chromatography, (4 g silica gel) eluting with 20%-80% EtOAc/Hex to give product (R)-2-(benzyloxy)-N'-(4-(4-chlorophenyl)-5-(4-cyanophenyl)-1-((2-methyl-6-(trifluoromethyl)pyridin-3-yl)methyl)-6-oxo-1,6-dihydropyridazin-3-yl)propanehydrazide as a beige solid (70 mg, 76% yield).

HPLC retention time 3.381 min (Method A); MS (M+1)=673.2.

Example 4B (R)-4-(3-(1-(benzyloxy)ethyl)-8-(4-chlorophenyl)-5-((2-methyl-6-(trifluoromethyl)pyridin-3-yl)methyl)-6-oxo-5,6-dihydro-[1,2,4]triazolo[4,3-b]pyridazin-7-yl)benzonitrile

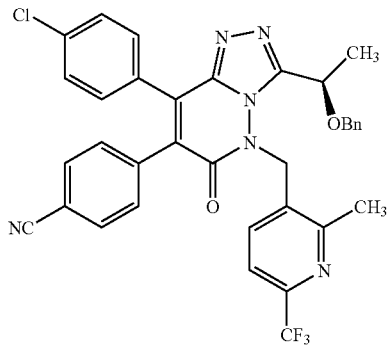

To a round bottom flask was added (R)-2-(benzyloxy)-N'-(4-(4-chlorophenyl)-5-(4-cyanophenyl)-1-((2-methyl-6-(trifluoromethyl)pyridin-3-yl)methyl)-6-oxo-1,6-dihydropyridazin-3-yl)propanehydrazide (70 mg, 0.140 mmol), toluene (3 ml). The reaction was heated to 120° C. POCl$_3$ (0.3 ml) was then added and the reaction was stirred at 120° C. for additional 3 hr. The reaction was then cooled to rt and the solution was concentrated. The resulting residue was diluted with EtOAc (30ml). The organic solution was then extracted with saturated NaHCO$_3$ (20 ml), water (20 ml) and saturated NaCl (20 ml). The organic solution was dried over MgSO$_4$, filtered and concentrated. The crude product was purified by silica gel column chromatography (4 g silica gel, 20%-50% EtOAc/Hex) to give product (R)-4-(3-(1-(benzyloxy)ethyl)-8-(4-chlorophenyl)-5-((2-methyl-6-(trifluoromethyl)pyridin-3-yl)methyl)-6-oxo-5,6-dihydro-[1,2,4]triazolo[4,3-b]pyridazin-7-yl)benzonitrile as a white solid (40 mg, 44% yield).

HPLC retention time 3.508 min (Method A); MS (M+1)=655.1.

Example 4C (R)-4-(8-(4-chlorophenyl)-3-(1-hydroxyethyl)-5-((2-methyl-6-(trifluoromethyl)pyridin-3-yl)methyl)-6-oxo-5,6-dihydro-[1,2,4]triazolo[4,3-b]pyridazin-7-yl)benzonitrile

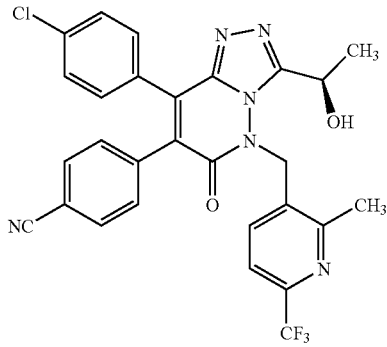

To a round bottom flask was added (R)-4-(3-(1-(benzyloxy)ethyl)-8-(4-chlorophenyl)-5-((2-methyl-6-(trifluoromethyl)pyridin-3-yl)methyl)-6-oxo-5,6-dihydro-[1,2,4]triazolo[4,3-b]pyridazin-7-yl)benzonitrile (40 mg, 0.061 mmol), CH$_3$CN (2 ml) and TMSI (244 mg, 1.22 mmol). The reaction was stirred at 60° C. under argon for 20 hr. After this time, the solution was cooled to rt and diluted with EtOAc (50 ml). The resulting organic solution was extracted with water (20 ml), 10% NaHSO$_3$ (20 ml) and saturated NaCl (20 ml). The organic layer was dried over MgSO$_4$, filtered and concentrated. The crude product was purified by silica gel column chromatography (8 g silica gel) eluting with a gradient of 20% to 80% EtOAc/Hex to give the product (R)-4-(8-(4-chlorophenyl)-3-(1-hydroxyethyl)-5-((2-methyl-6-(trifluoromethyl)pyridin-3-yl)methyl)-6-oxo-5,6-dihydro-[1,2,4]triazolo[4,3-b]pyridazin-7-yl)benzonitrile as a white solid (15 mg, 44% yield).

HPLC retention time 3.053 min (Method A); MS (M+1)=565.1;

$^1$HNMR (CDCl$_3$, 500 Hz) 7.60(d, 2H, J=8.25 Hz), 7.52(d, 1H, J=8.25 Hz), 7.32-7.38(m, 7H), 5.95-6.15(2H, ABAB), 4.5(m, 1H), 2.75(s, 3H), 2.34(d, 1H, J=9.9 Hz), 1.84(d, 3H, J=6.6 Hz).

Example 5

Preparation of (S)-4-(8-(4-chlorophenyl)-3-(1-hydroxyethyl)-5-((2-methyl-6-(trifluoromethyl)pyridin-3-yl)methyl)-6-oxo-5,6-dihydro-[1,2,4]triazolo[4,3-b]pyridazin-7-yl)benzonitrile

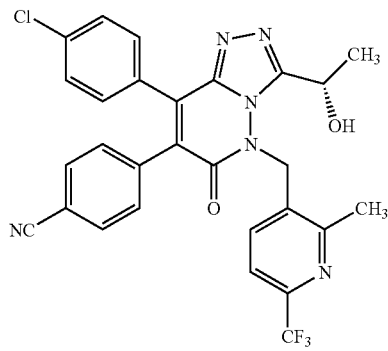

Example 5A (S)-2-(benzyloxy)-N'-(4-(4-chlorophenyl)-5-(4-cyanophenyl)-1-((2-methyl-6-(trifluoromethyl)pyridin-3-yl)methyl)-6-oxo-1,6-dihydropyridazin-3-yl)propanehydrazide

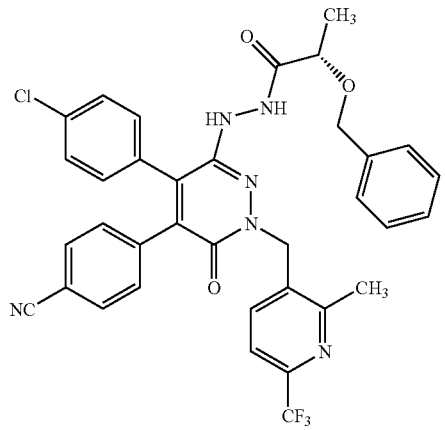

To a round bottom flask was added 4-(5-(4-chlorophenyl)-6-hydrazinyl-2-((2-methyl-6-(trifluoromethyl)pyridin-3-yl)methyl)-3-oxo-2,3-dihydropyridazin-4-yl)benzonitrile (70 mg, 0.1367 mmol), prepared as described in Example 2B, (S)-2-(benzyloxy)propanoic acid (25 mg, 0.1367 mmol), EDAC (30 mg, 0.15 mmol), HOBT (20.3 mg, 0.15 0 mmol), THF (5 ml) and diisopropyl ethyl amine (19.4 mg, 0.15 mmol). The reaction was stirred at rt for 5 hr. After this time, the reaction was diluted with EtOAc (40 ml). The resulting solution was extracted with water (2×20 ml), and saturated NaCl (20 ml). The organic layer was dried over MgSO$_4$, filtered and concentrated. The crude product was purified by silica gel column chromatography (4 g silica gel) eluting with a gradient of 0%-60% EtOAc/Hex to give product (S)-2-

(benzyloxy)-N'-(4-(4-chlorophenyl)-5-(4-cyanophenyl)-1-((2-methyl-6-(trifluoromethyl)pyridin-3-yl)methyl)-6-oxo-1,6-dihydropyridazin-3-yl)propanehydrazide as a beige solid (70 mg, 76% yield).

HPLC retention time 3.381 min (Method A); MS (M+1)=673.0.

Example 5B (S)-4-(3-(1-(benzyloxy)ethyl)-8-(4-chlorophenyl)-5-((2-methyl-6-(trifluoromethyl)pyridin-3-yl)methyl)-6-oxo-5,6-dihydro-[1,2,4]triazolo[4,3-b]pyridazin-7-yl)benzonitrile

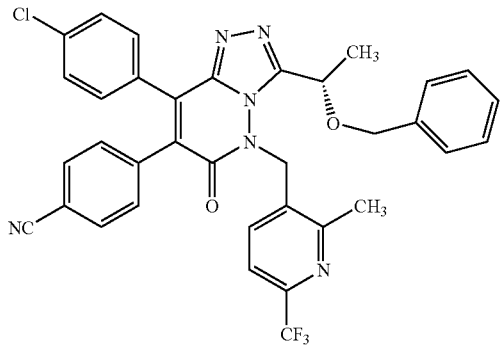

To a round bottom flask was added (S)-2-(benzyloxy)-N'-(4-(4-chlorophenyl)-5-(4-cyanophenyl)-1-((2-methyl-6-(trifluoromethyl)pyridin-3-yl)methyl)-6-oxo-1,6-dihydropyridazin-3-yl)propanehydrazide (70 mg, 0.140 mmol) and toluene (3 ml). The reaction was heated to 120° C. Then POCl₃ (0.3 ml) was added and the reaction was stirred at 120° C. for additional 3 hr. After this time, the solution was cooled to rt and concentrated. The residue was diluted with EtOAc (30 ml) and washed with NaHCO₃(sat, 20 ml), water (20 ml) and saturated NaCl (20 ml). The organic solution was dried over MgSO₄, filtered and concentrated. The crude product was purified by silica gel column chromatography (4 g silica gel) eluting with a gradient of 20%-50% EtOAc/Hex to give product (S)-4-(3-(1-(benzyloxy)ethyl)-8-(4-chlorophenyl)-5-((2-methyl-6-(trifluoromethyl)pyridin-3-yl)methyl)-6-oxo-5,6-dihydro-[1,2,4]triazolo[4,3-b]pyridazin-7-yl)benzonitrile as a white solid (40 mg, 44% yield).

HPLC retention time 3.513 min (Method A); MS (M+1)=655.0.

Example 5C (S)-4-(8-(4-chlorophenyl)-3-(1-hydroxyethyl)-5-((2-methyl-6-(trifluoromethyl)pyridin-3-yl)methyl)-6-oxo-5,6-dihydro-[1,2,4]triazolo[4,3-b]pyridazin-7-yl)benzonitrile

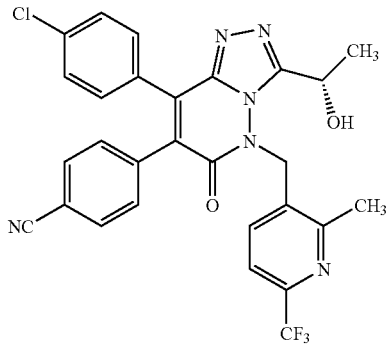

To a round bottom flask was added (S)-4-(3-(1-(benzyloxy)ethyl)-8-(4-chlorophenyl)-5-((2-methyl-6-(trifluoromethyl)pyridin-3-yl)methyl)-6-oxo-5,6-dihydro-[1,2,4]triazolo[4,3-b]pyridazin-7-yl)benzonitrile (30 mg, 0.0458 mmol), CH₃CN (2 ml) and TMSI (244 mg, 1.22 mmol). The reaction was stirred at 60° C. under argon for 4 days. After this time, the reaction mixture was with EtOAc (50 ml). The resulting organic solution was wash with water (20 ml), 10% NaHSO₃(20 ml) and saturated NaCl (20 ml). The organic layer was dried over MgSO₄, filtered and concentrated. The crude product was purified by silica gel column chromatography (8 g silica gel) eluting with a gradient of 0-80% EtOAc/Hex to give product (R)-4-(8-(4-chlorophenyl)-3-(1-hydroxyethyl)-5-((2-methyl-6-(trifluoromethyl)pyridin-3-yl)methyl)-6-oxo-5,6-dihydro-[1,2,4]triazolo[4,3-b]pyridazin-7-yl)benzonitrile as a white solid (8 mg, 31% yield).

HPLC retention time 3.020 min (Method A); MS (M+1)=565.0;
¹HNMR (CDCl₃, 500 Hz) 7.60(d, 2H, J=8.25 Hz), 7.52(d, 1H, J=8.25 Hz), 7.32-7.38(m, 7H), 5.96-6.15(ABq, 2H), 4.53 (m, 1H), 2.75(s, 3H), 2.31(d, 1H, J=9.35 Hz), 1.84(d, 3H, J=6.05 Hz).

Example 6

Preparation of Sodium (8-(4-chlorophenyl)-7-(4-cyanophenyl)-5-((2-methyl-6-(trifluoromethyl)pyridin-3-yl)methyl)-6-oxo-5,6-dihydro-[1,2,4]triazolo[4,3-b]pyridazin-3-yl)methyl hydrogenphosphate

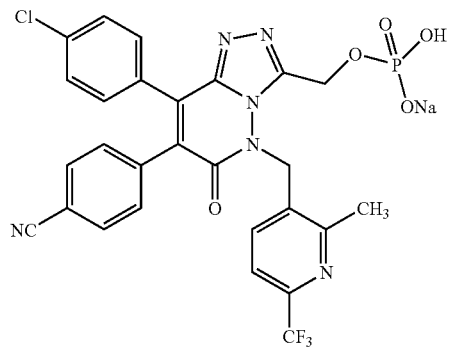

To a round bottom flask was added 4-(8-(4-chlorophenyl)-3-(hydroxymethyl)-5-((2-methyl-6-(trifluoromethyl)pyridin-3-yl)methyl)-6-oxo-5,6-dihydro-[1,2,4]triazolo[4,3-b]pyridazin-7-yl)benzonitrile (25 mg, 0.0454 mmol), di-tert-butyl diethylphosphoramidite (34 mg, 0.136 mmol), 1,2,4-triazole (9.5 mg, 0.136 mmol) and 1,2-dichloroethane (3 ml). The reaction was stirred at 60° C. for 24 hr. After this time the reaction was cooled to rt. H₂O₂(7 N, 0.5 ml) was then added and the reaction was stirred at rt for 60 min. Na₂SO₃ (10%, 1 ml) was added and the reaction was stirred at rt for an additional 30 min. After this time, the reaction mixture was concentrated. The residue was diluted with EtOAc (50 ml) and the resulting solution was washed with water (25 ml) and saturated NaCl (25 ml). The organic layer was dried over MgSO₄, filtered and concentrated. The crude intermediate was purified by silica gel column chromatography (4 g silica gel) eluting with a gradient of 0-50% EtOAc/Hex to give di-tert-butyl (8-(4-chlorophenyl)-7-(4-cyanophenyl)-5-((2-methyl-6-(trifluoromethyl)pyridin-3-yl)methyl)-6-oxo-5,6-dihydro-[1,2,4]triazolo[4,3-b]pyridazin-3-yl)methyl phosphate as clear oil. To this purified intermediate was added CH₂Cl₂(2 ml) and TFA (0.5 ml). The reaction was stirred at rt for 10 min. After this time the solution was concentrated. The crude product was purified by preparative HPLC eluting with water/MeOH to give the product (28 mg). The product was then dissolved in water (1 ml) and 1N NaOH (1N, 0.0445 mmol) was added. The resulting solution was concentrated on a lyophilizer to give the title compound, sodium (8-(4-chlorophenyl)-7-(4-cyanophenyl)-5-((2-methyl-6-(trifluoromethyl)pyridin-3-yl)methyl)-6-oxo-5,6-dihydro-[1,2,4]triazolo[4,3-b]pyridazin-3-yl)methyl hydrogenphosphate, as a white solid (29 mg, 94%).

HPLC retention time 3.573 min (Method A); MS (M+1)=631.1 (as free acid)

$^1$HNMR (CD$_3$OD, 500 Hz) 7.83(d, 1H, J=7.7 Hz (, 7.66(d, 2H, J=8.25 Hz), 7.63(d, 1H, J=7.7 Hz), 7.42(d, 2H, J=8.25 Hz), 7.39(s, 4H), 5.87(s, 2H), 5.03(d, 2H), 2.76(s, 3H)

Example 7

Preparation of (S)—((S)-1-(8-(4-chlorophenyl)-5-((2-methyl-6-(trifluoromethyl)pyridin-3-yl)methyl)-6-oxo-7-phenyl-5,6-dihydro-[1,2,4]triazolo[4,3-b]pyridazin-3-yl)ethyl) 2-amino-3-methylbutanoate

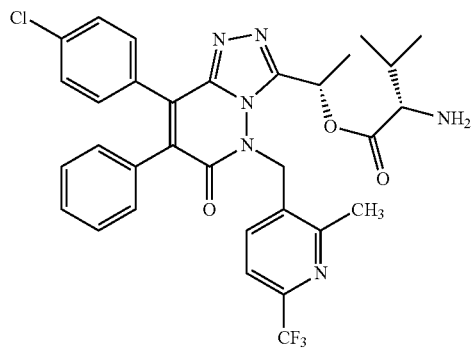

Example 7A (S)—((S)-1-(8-(4-chlorophenyl)-5-((2-methyl-6-(trifluoromethyl)pyridin-3-yl)methyl)-6-oxo-7-phenyl-5,6-dihydro-[1,2,4]triazolo[4,3-b]pyridazin-3-yl)ethyl) 2-(tert-butoxycarbonylamino)-3-methylbutanoate

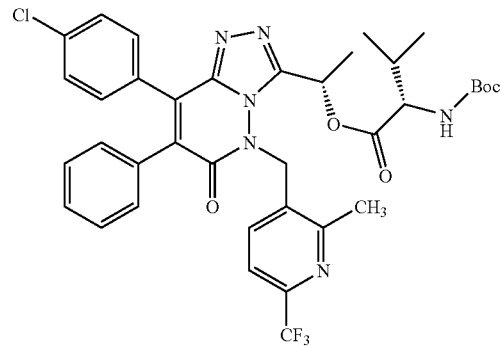

To a round bottom flask was added (S)-8-(4-chlorophenyl)-3-(1-hydroxyethyl)-5-((2-methyl-6-(trifluoromethyl)pyridin-3-yl)methyl)-7-phenyl-[1,2,4]triazolo[4,3-b]pyridazin-6(5H)-one (35 mg, 0.0648 mmol), Boc-L-Valine (15.5 mg, 0.0713 mmol), CH$_2$Cl$_2$(3 ml), DMAP (cat, 3 mg) and DIC (12.3 mg, 0.0973 mmol). The reaction was stirred at rt for 30 min. After this time, the solution was concentrated. The crude product was purified by silica gel column chromatography (8 g silica gel) eluting with a gradient of 0-50% EtOAc/Hex to give product (S)—((S)-1-(8-(4-chlorophenyl)-5-((2-methyl-6-(trifluoromethyl)pyridin-3-yl)methyl)-6-oxo-7-phenyl-5,6-dihydro-[1,2,4]triazolo[4,3-b]pyridazin-3-yl)ethyl) 2-(tert-butoxycarbonylamino)-3-methylbutanoate, as a white solid (39 mg, 81% yield).

HPLC retention time 3.853 min (Method A); MS (M+1)=739.1.

Example 7B (S)—((S)-1-(8-(4-chlorophenyl)-5-((2-methyl-6-(trifluoromethyl)pyridin-3-yl)methyl)-6-oxo-7-phenyl-5,6-dihydro-[1,2,4]triazolo[4,3-b]pyridazin-3-yl)ethyl) 2-amino-3-methylbutanoate

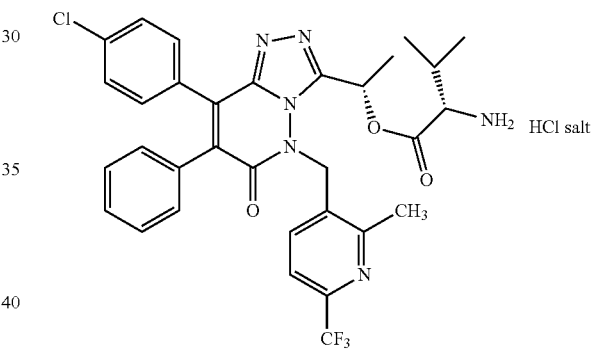

To a round bottom flask was added (S)—((S)-1-(8-(4-chlorophenyl)-5-((2-methyl-6-(trifluoromethyl)pyridin-3-yl)methyl)-6-oxo-7-phenyl-5,6-dihydro-[1,2,4]triazolo[4,3-b]pyridazin-3-yl)ethyl) 2-(tert-butoxycarbonylamino)-3-methylbutanoate (39 mg, 0.529 mmol) and 4N HCl (2 ml). The reaction was stirred at rt for 30 min. After this time, the solution was concentrated under reduced pressure. To the residue was added CH$_2$Cl$_2$(2 ml) and hexanes (2 ml). The solvent was decanted. The remaining solid was dried under vacuum to give product (S)—((S)-1-(8-(4-chlorophenyl)-5-((2-methyl-6-(trifluoromethyl)pyridin-3-yl)methyl)-6-oxo-7-phenyl-5,6-dihydro-[1,2,4]triazolo[4,3-b]pyridazin-3-yl)ethyl) 2-amino-3-methylbutanoate as an HCl salt (30mg, 85% yield).

HPLC retention time 2.821 min (Method A); MS (M+1)=639.1;

$^1$HNMR (CD$_3$OD, 500 Hz) 8.00(d, 1H, J=8.25 Hz), 7.69(d, 1H, J=7.7 Hz), 7.34(m, 4H), 7.29(m, 3H), 7.23(m, 2H), 5.71-5.81(m, 2H), 4.00(m, 1H), 2.71(s, 3H), 1.60(d, 3H, J=6.6 Hz), 0.95-1.1(m, 8H).

Examples 8-9

The following prodrugs were prepared according to the methods described above for Example 7.

| Example # | HPLC retention time (min) (Method A) | MS (M + 1) | ¹HNMR (CD₃OD, 500 Hz) |
|---|---|---|---|
| Example 8: (S)-((S)-1-(8-(4-chlorophenyl)-5-((2-methyl-6-(trifluoromethyl)pyridin-3-yl)methyl)-6-oxo-7-p-tolyl-5,6-dihydro-[1,2,4]triazolo[4,3-b]pyridazin-3-yl)ethyl) 2-aminopropanoate | 2.906 | 625.1 | 7.96 (d, 1H, J = 8.25 Hz), 7.69 (d, 1H, J = 8.25), 7.35 (s, 4H), 7.10 (s, 4H), 5.75 (m, 3H), 4.13 (m, 1H), 2.71 (s, 3H), 2.31 (s, 3H), 1.60 (d, 3H, J = 6.6 Hz), 1.50 (d, 3H, J = 7.15 Hz) |
| Example 9: (S)-((S)-1-(7-(4-chlorophenyl)-5-((2-methyl-6-(trifluoromethyl)pyridin-3-yl)methyl)-6-oxo-8-p-tolyl-5,6-dihydro-[1,2,4]triazolo[4,3-b]pyridazin-3-yl)ethyl) 2-aminopropanoate | 2.921 | 625.1 | 7.96 (d, 1H, J = 7.15 Hz), 7.68 (d, 1H, J = 7.15 Hz), 7.26 (t, 4H), 7.19 (t, 4H), 5.73 (m, 3H), 4.12 (m, 1H), 2.70 (s, 3H), 2.5 (s, 3H), 1.59 (d, 3H, J = 6.05 Hz) |

Example 10

Preparation of 4-(8-(4-chlorophenyl)-3-((dimethylamino)methyl)-5-((2-methyl-6-(trifluoromethyl)pyridin-3-yl)methyl)-6-oxo-5,6-dihydro-[1,2,4]triazolo[4,3-b]pyridazin-7-yl)benzonitrile

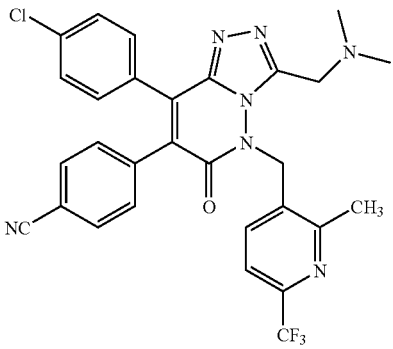

Example 10A

N'-(4-(4-chlorophenyl)-5-(4-cyanophenyl)-1-((2-methyl-6-(trifluoromethyl)pyridin-3-yl)methyl)-6-oxo-1,6-dihydropyridazin-3-yl) -2-(dimethylamino)acetohydrazide

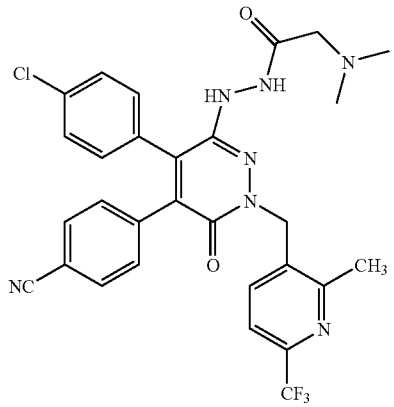

To a round bottom flask was added 4-(5-(4-chlorophenyl)-6-hydrazinyl-2-((2-methyl-6-(trifluoromethyl)pyridin-3-yl)methyl)-3-oxo-2,3-dihydropyridazin-4-yl)benzonitrile (100 mg, 0.195 mmol), THF (3 ml), Et₃B (0.109 ml, 0.781 mmol) and dimethylaminoacetyl chloride. The reaction was stirred at rt overnight. After this time, the solution was diluted with EtOAc (35 ml). The resulting solution was washed with water (2×100 ml) and saturated NaCl (10 ml). The organic layer was dried over MgSO₄, filtered and concentrated. The residue was purified by silica gel column chromatography (4 g, silica gel) eluting with a gradient of 0-100% EtOAc/CH₂Cl₂ to give product N'-(4-(4-chlorophenyl)-5-(4-cyanophenyl)-1-((2-methyl-6-(trifluoromethyl)pyridin-3-yl)methyl)-6-oxo-1,6-dihydropyridazin-3-yl)-2-(dimethylamino)acetohydrazide as a yellow solid (40 mg, 37% yield).

HPLC retention time 2.370 min (Method A).

Example 10B 4-(8-(4-chlorophenyl)-3-((dimethylamino)methyl)-5-((2-methyl-6-(trifluoromethyl)pyridin-3-yl)methyl)-6-oxo-5,6-dihydro-[1,2,4]triazolo[4,3-b]pyridazin-7-yl)benzonitrile

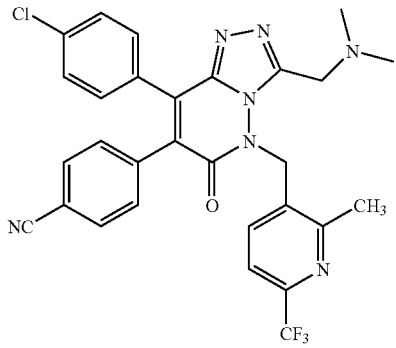

To a round bottom flask was added N'-(4-(4-chlorophenyl)-5-(4-cyanophenyl)-1-((2-methyl-6-(trifluoromethyl)pyridin-3-yl)methyl)-6-oxo-1,6-dihydropyridazin-3-yl)-2-(dimethylamino)acetohydrazide (25 mg, 0.0446 mmol) and toluene (3 ml). The reaction was stirred at 120° C. for 15 min. Then POCl₃ (0.3 ml) was added and the reaction was stirred at 120° C. for additional 40 min. After this time, the solution was cooled to rt and the reaction mixture was concentrated. The residue was partitioned between EtOAc (30 ml) and NaHCO₃ (sat, 20 ml). The organic layer was separated and washed with water (10 ml) and saturated NaCl (10 ml). The organic layer was then dried over MgSO₄, filtered and concentrated. The crude product was purified by silica gel column chromatography (4 g silica gel) eluting with a gradient of 0-80% EtOAc/CH₂Cl₂ to give product 4-(8-(4-chlorophenyl)-3-((dimethylamino)methyl)-5-((2-methyl-6-(trifluoromethyl)pyridin-3-yl)methyl)-6-oxo-5,6-dihydro-[1,2,4]triazolo[4,3-b]pyridazin-7-yl)benzonitrile as an off white solid (10 mg, 39% yield).

HPLC retention time 2.545 min (Method A); MS (M+1)=578.1;

¹HNMR (CDCl₃, 500 Hz) 7.58(d, 2H, J=8.25 Hz), 7.53(d, 1H, J=7.7), 7.31-7.38(m, 7H), 6.29(s, 2H), 3.51(s, 2H), 2.73 (s, 3H), 2.21(s, 6H).

Example 11

Preparation of 4-(3-(aminomethyl)-8-(4-chlorophenyl)-5-((2-methyl-6-(trifluoromethyl)pyridin-3-yl)methyl)-6-oxo-5,6-dihydro-[1,2,4]triazolo[4,3-b]pyridazin-7-yl)benzonitrile

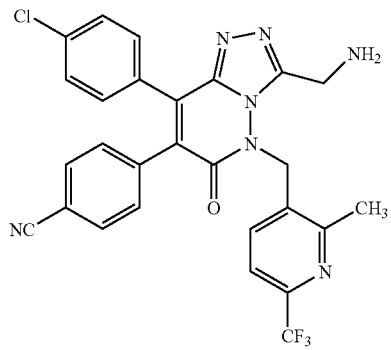

Example 11A tert-butyl 2-(2-(4-(4-chlorophenyl)-5-(4-cyanophenyl)-1-((2-methyl-6-(trifluoromethyl)pyridin-3-yl)methyl)-6-oxo-1,6-dihydropyridazin-3-yl)hydrazinyl)-2-oxoethylcarbamate

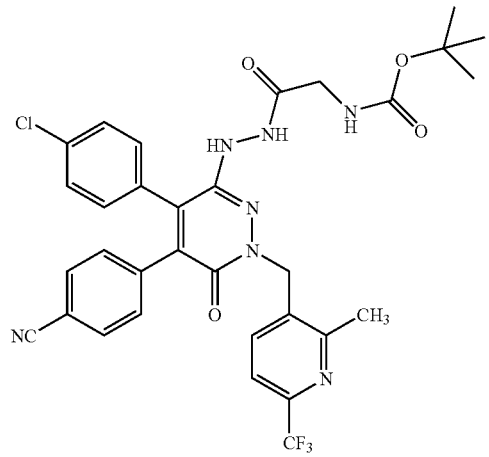

To a round bottom flask was added 4-(5-(4-chlorophenyl)-6-hydrazinyl-2-((2-methyl-6-(trifluoromethyl)pyridin-3-yl)methyl)-3-oxo-2,3-dihydropyridazin-4-yl)benzonitrile (70 mg, 0.1367 mmol), N-Boc-alanine (24 mg, 0.1367 mmol), EDAC (30 mg, 0.150 mmol), HOBT (20.3 mg, 0.150 mmol) THF (5 ml) and diisopropyl ethyl amine (0.026 ml, 0.150 mmol). The reaction was stirred at rt for 5 hr. After this time the reaction mixture was diluted with EtOAc (25 ml). The resulting solution was washed with water (2×15 ml) and saturated NaCl (15 ml). The organic layer was dried over $MgSO_4$, filtered and concentrated. The crude product was purified by silica gel column chromatography (8 g silica gel) eluting with a gradient of 20%-100% EtOAc/Hex to give product tert-butyl 2-(2-(4-(4-chlorophenyl)-5-(4-cyanophenyl)-1-((2-methyl-6-(trifluoromethyl)pyridin-3-yl)methyl)-6-oxo-1,6-dihydropyridazin-3-yl)hydrazinyl)-2-oxoethylcarbamate as a light yellow solid (54 mg, 60% yield)

HPLC retention time 3.241 min (Method A); MS (M+1)=668.1.

Example 11B 4-(3-(aminomethyl)-8-(4-chlorophenyl)-5-((2-methyl-6-(trifluoromethyl)pyridin-3-yl)methyl)-6-oxo-5,6-dihydro-[1,2,4]triazolo[4,3-b]pyridazin-7-yl)benzonitrile

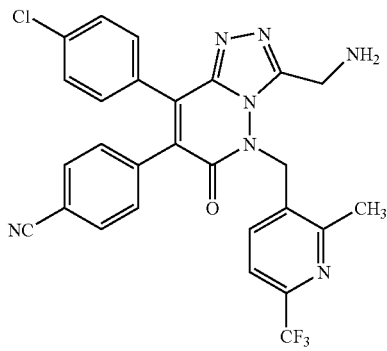

To a round bottom flask was added tert-butyl 2-(2-(4-(4-chlorophenyl) -5-(4-cyanophenyl)-1-((2-methyl-6-(trifluoromethyl)pyridin-3-yl)methyl)-6-oxo-1,6-dihydropyridazin-3-yl)hydrazinyl)-2-oxoethylcarbamate (54 mg, 0.0808 mmol), acetonitrile (3 ml), and tetra-chloro-1,2-dibromoethane (58 mg, 0.178 mmol). The reaction was cooled to 0° C. Triphenylphosphine (47 mg, 0.178 mmol) was then added and the reaction was stirred at 0° C. for 5 min. After this time, $Et_3N$ (0.05 ml, 0.356 mmol) was added to the reaction. The reaction was slowly warmed up to rt and stirred for 16 hrs. After this time, the reaction was diluted with EtOAc (25 ml). The resulting solution was washed with water (2×20 ml) and saturated NaCl (20 ml). The organic layer was dried over $MgSO_4$, filtered and concentrated. The crude product was purified by silica gel column chromatography (8 gm silica gel) eluting with a gradient of 20%-80% EtOAc/Hex to give the cyclized intermediate. This material was then dissolved in $CH_2Cl_2$(1 ml) and TFA (1 ml) was added. The reaction was stirred at rt for 1 hr. After this time, the solvent was removed. The residue was diluted with EtOAc (20 ml). The resulting solution was washed with saturated $NaHCO_3$(20 ml), water (10 ml) and saturated NaCl (10 ml). The organic layer was dried over $MgSO_4$, filtered and concentrated. The crude product was purified by silica gel column chromatography (4 g silica gel) eluting with a gradient of 100% EtOAc and then 5% $MeOH/CH_2Cl_2$ to give product as a white solid (15 mg, 34% yield).

HPLC retention time 2.383 min (Method A); MS (M+1)=550.0;
$^1HNMR$ ($CDCl_3$, 500 Hz) 7.59(d, 2H, J=8.25 Hz), 7.52(d, 2H, J=7.7 Hz), 7.32-7.41(m, 7H), 6.30(m, 2H), 3.99(s, 2H), 3.73(s, 3H).

Examples 12-17

The following compounds were prepared according to the methods described above for Examples 10 or 11.

| | Retention time (Method A) | LCMS (M + 1) | $^1HNMR$ ($CDCl_3$, 500 Hz) |
|---|---|---|---|
| Example 12: 3-(aminomethyl)-8-(4-chlorophenyl)-5-((2-methyl-6-(trifluoromethyl)pyridin-3-yl)methyl)-7-phenyl-[1,2,4]triazolo[4,3-b]pyridazin-6(5H)-one | 2.633 min | 525.0 | 7.52 (d, 1H, J = 8.25 Hz), 7.42 (d, 1H, J = 7.7 Hz), 7.28-7.37 (m, 7H), 7.19 (m, 2H), 6.30 (s, 2H), 3.94 (s, 2H), 2.74 (s, 3H) |

|   | Retention time (Method A) | LCMS (M + 1) | ¹HNMR (CDCl₃, 500 Hz) |
|---|---|---|---|
| Example 13: 3-(aminomethyl)-8-(4-chlorophenyl)-5-((2-methyl-6-(trifluoromethyl)pyridin-3-yl)methyl)-7-p-tolyl-[1,2,4]triazolo[4,3-b]pyridazin-6(5H)-one | 2.793 min | 539.1 | 7.44 (d, 2H, J = 8.25 Hz), 7.34 (d, 2H, J = 7.7 Hz), 7.28 (d, 2H, J = 8.8 Hz), 7.23 (d, 2H, J = 8.25 Hz), 6.99-7.04 (m, 4H), 6.17 (s, 2H), 3.88 (s, 2H), 2.66 (s, 3H), 2.25 (s, 3H) |
| Example 14: 8-(4-chlorophenyl)-5-((2-methyl-6-(trifluoromethyl)pyridin-3-yl)methyl)-3-((methylamino)methyl-7-phenyl-[1,2,4]triazolo[4,3-b]pyridazin-6(5H)-one | 2.365 min | 539.0 | 7.52 (d, 2H, J = 8.25 Hz), 7.42 (d, 2H, J = 7.7 Hz), 7.37 (d, 2H, J = 8.25 Hz), 7.28-7.33 (m, 5H), 7.18 (m, 2H), 6.28 (s, 2H), 3.75 (s, 2H), 2.73 (s, 3H), 2.42 (s, 3H) |
| Example 15: 3-(aminomethyl)-7,8-bis(4-chlorophenyl)-5-((2-methyl-6-(trifluoromethyl)pyridin-3-yl)methyl)-[1,2,4]triazolo[4,3-b]pyridazin-6(5H)-one | 2.946 min | 559.0 | 7.65-7.69 (m, 1H), 7.51-7.55 (m, 2H), 7.45-7.48 (m, 1H), 7.40 (d, 1H, J = 7.7 Hz), 7.26-7.28 (m, 3H), 7.14 (d, 2H, J = 8.25 Hz), 6.28 (s, 2H), 3.95 (s, 2H), 2.74 (s, 3H) |

| | Retention time (Method A) | LCMS (M + 1) | ¹HNMR (CDCl₃, 500 Hz) |
|---|---|---|---|
| Example 16: (S)-3-(1-aminoethyl)-8-(4-chlorophenyl)-5-((2-methyl-6-(trifluoromethyl)pyridin-3-yl)methyl)-7-p-tolyl-[1,2,4]triazolo[4,3-b]pyridazin-6(5H)-one | 3.105 min | 553.1 | CD3OD, 500 Hz 7.88 (d, 1H, J = 7.7 Hz), 7.71 (d, 1H, J = 7.7 Hz), 7.36 (s, 4H), 7.11 (s, 4H), 5.53-5.83 (ABq, 2H), 4.36 (m, 1H), 2.74 (s, 3H), 2.31 (s, 3H) |
| Example 17: 3-(aminomethyl)-7-(4-chlorophenyl)-5-((2-methyl-6-(trifluoromethyl)pyridin-3-yl)methyl)-8-p-tolyl-[1,2,4]triazolo[4,3-b]pyridazin-6(5H)-one | 3.006 | 539.2 | CD3OD, 500 Hz 7.76 (d, 1H, J = 8.25 Hz), 7.61 (d, 1H, J = 7.7 Hz), 7.18 (m, 4H), 7.11 (m, 4H), 5.62 (s, 2H), 4.24 (s, 2H), 2.66 (s, 3H), 2.26 (s, 3H) |

Example 18

Preparation of (S)-7-(4-chlorophenyl)-3-(1-hydroxyethyl)-5-((2-methyl-6-(trifluoromethyl)pyridin-3-yl)methyl)-8-p-tolyl-[1,2,4]triazolo[4,3-b]pyridazin-6(5H)-one

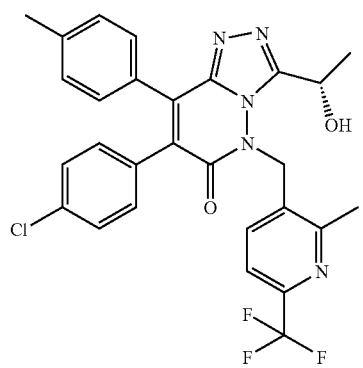

The title compound was prepared using methods similar to those described for the preparation of Example 4.

HPLC retention time 3.509 min (Method A), MS (M+1)=554.1;

¹HNMR (CD₃OD, 500 Hz) 7.38(d, 1H, J=7.7 Hz), 7.26(d, 1H, J=7.7 Hz), 7.14(m, 4H), 7.02(m, 4H), 5.74-5.99(Abq, 2H), 4.35(m, 1H), 2.60(s, 3H), 2.24(s, 3H), 1.65(d, 3H), J=6.1 Hz).

Example 19

Preparation of (S)-8-(4-chlorophenyl)-3-(1-hydroxyethyl)-5-((2-methyl-6-(trifluoromethyl)pyridin-3-yl)methyl)-7-p-tolyl-[1,2,4]triazolo[4,3-b]pyridazin-6(5H)-one

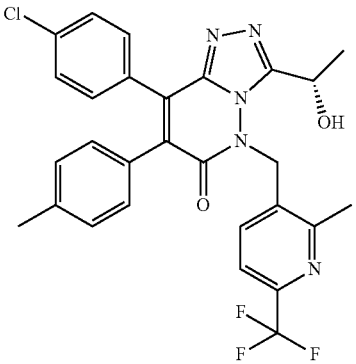

The title compound was prepared using methods similar to those described for the preparation of Example 4.

HPLC retention time 3.818min (Method A), MS (M+1)=554.1;

$^1$HNMR (CD$_3$OD, 500 Hz) 7.76(d, 1H, J=8.25 Hz), 7.61(d, 1H, J=7.7 Hz), 7.35-7.36(m, 4H), 7.09(m, 4H), 5.89-6.29 (Abq, 2H), 4.54(m, 1H), 2.70(s, 3H), 2.29(s, 3H), 1.67(d, 3H), J=6.1 Hz).

Example 20

Preparation of (S)-8-(4-chlorophenyl)-3-(1-hydroxy-ethyl)-5-((2-methyl-6-(trifluoromethyl)pyridin-3-yl) methyl)-7-phenyl-[1,2,4]triazolo[4,3-b]pyridazin-6 (5H)-one

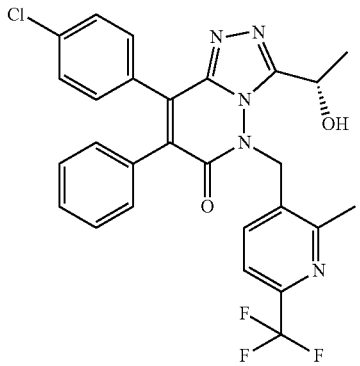

The title compound was prepared using methods similar to those described for the preparation of Example 4.

HPLC retention time 2.981min (Method A), MS (M+1)=540.1;

$^1$HNMR (CD$_3$OD, 500 Hz) 7.51(d, 1H, J=8.25 Hz), 7.40(d, 1H, J=7.7 Hz), 7.26-7.35(m, 7H), 7.19(m, 2H), 5.94-6.12 (Abq, 2H), 4.50(m, 1H), 2.74(s, 3H), 1.81(d, 3H, J=6.6 Hz).

Example 21

Preparation of (R)-8-(4-chlorophenyl)-3-(1-hydroxy-ethyl)-5-((2-methyl-6-(trifluoromethyl)pyridin-3-yl) methyl)-7-phenyl-[1,2,4]triazolo[4,3-b]pyridazin-6 (5H)-one

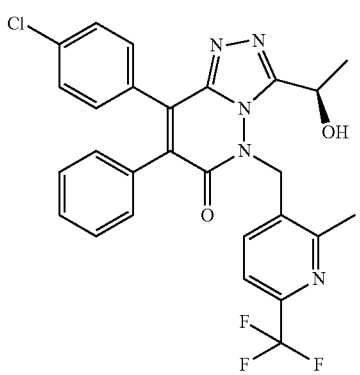

The title compound was prepared using methods similar to those described for the preparation of Example 4.

HPLC retention time 2.975min (Method A), MS (M+1)=540.0;

$^1$HNMR (CD$_3$OD, 500 Hz) 7.50(d, 1H, J=8.25 Hz), 7.39(d, 1H, J=7.7 Hz), 7.24-7.34(m, 7H), 7.17(m, 2H), 5.92-6.11 (Abq, 2H), 4.50(m, 1H), 2.73(s, 3H), 1.79(d, 3H, J=6.6 Hz).

Example 22

Preparation of 8-(4-chlorophenyl)-3-(methoxymethyl)-5-((2-methyl-6-(trifluoromethyl)pyridin-3-yl) methyl)-7-phenyl-[1,2,4]triazolo[4,3-b]pyridazin-6 (5H)-one

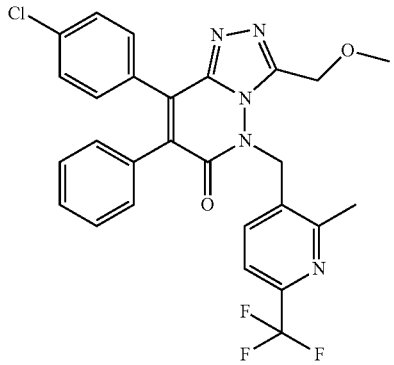

The title compound was prepared using methods similar to those described for the preparation of Example 2.

HPLC retention time 3.090min (Method A), MS (M+1)=540.0;

$^1$HNMR (CD$_3$OD, 500 Hz) 7.51(d, 1H, J=7.7 Hz), 7.28-7.37(m, 8H), 7.20(m, 2H), 5.95(s, 2H), 4.45(s, 2H), 3.38(s, 3H), 3.74(s, 3H).

Biological Evaluation

Cannabinoid Receptor Binding Assay

Radioligand binding studies were conducted in membranes prepared from Chinese Hamster Ovary (CHO) cells that over-express recombinant human CB-1 (CHO-CB-1 cells). Total assay volume for the binding studies was 100 μl. 5 μg of membranes were brought up to a final volume of 95 μl with Binding Buffer (25 mM HEPES, 150 mM NaCl, 2.5 mM CaCl$_2$, 1 mM MgCl$_2$, 0.25% BSA). The diluted membranes were preincubated with a compound or DMSO vehicle. The binding reaction was initiated by the addition of 2 nM final $^3$H-CP-55,940 (120 Ci/mmol) and proceeded for 2.5 hours at room temperature. The binding reaction was terminated by transferring the reaction to GF/B 96 well plates (presoaked with 0.3% polyethylenimine) using a Packard Cell Harvester. The filter was washed with 0.25 ×PBS, 30 μl MicroScint was added per well, and the bound radiolabel was quantitated by scintillation counting on a Packard TopCount Scintillation Counter. The CB-2 radioligand binding assay was conducted identically except that the membranes from CHO-CB-2 cells were used.

For a compound to be considered a CB-1 antagonist, the compound must possess a CB-1 receptor binding affinity Ki less than 13000 nM. As determined by the assay described above, the CB-1 receptor binding K$_i$ values of working Examples 1-63 fall within the range of 0.01 nM to 10000 nM.

Cannabinoid Receptor Functional Activity Assay

Functional CB-1 inverse agonist activity of test compounds was determined in CHO-CB-1 cells using a cAMP accumulation assay. CHO-CB-1 cells were grown in 96 well plates to near confluence. On the day of the functional assay, growth medium was aspirated and 100 of Assay Buffer (PBS plus 25 mM HEPES/0.1 mM 3-isobutyl-1-methylxanthine/ 0.1% BSA) was added. Compounds were added to the Assay buffer diluted 1:100 from 100% DMSO and allowed to pre-incubate for 10 minutes prior to addition of 5 uM forskolin. The mixture was allowed to proceed for 15 minutes at room temperature and was terminated by the addition of 0.1 N HCl. The total intracellular cAMP concentration was quantitated using the Amersham cAMP SPA kit.

Canine Half-Life Assay

Functional canine half-life of test compounds was determined by methods none to one of ordinary skill in the art. For example, pharmacokinetic parameters were determined in male beagle dogs (weight of 12.4, 13.2 and 8.9 kg). The intravenous ("IV") solution dose studies were conducted in a crossover design (n=3). Animals with vascular access ports, chronically implanted in the femoral vein, were used for administration of the dose. The animals had free access to water and were conscious and unrestrained throughout the study. In the IV study, drug was infused at a dose of 1 mg/kg (1 mL/kg) in 50% PEG-400, 10% ethanol and 40% water over 10 minutes. Serial blood samples were collected from the jugular vein at 0.167, 0.25, 0.5, 0.75, 1, 2, 4, 6, 8, 24, 48 and 72 hours post-dose. Plasma was prepared immediately, and the samples were frozen on dry ice and stored at −20° C. until analysis. All samples were analyzed for the concentration of the parent drug by LC-MS/MS analysis.

The pharmacokinetic parameters were calculated by Non-Compartmental Analysis using the KINETICA™ software program (version 4.2, InnaPhase Co., Philadelphia, Pa.). The AUC0-Tlast and AUCtot values were calculated using the trapezoidal summations. The elimination half-life (T1/2) was calculated from the terminal, linear portion of the plasma concentration-time data curve. The total clearance (CLplasma), mean residence time (MRT), and the steady state volume of distribution (Vss) were also calculated after intravenous administration. The total blood clearance (CLblood) was calculated by using the total plasma clearance and the blood to plasma concentration ratio. All results are expressed as mean±SD, unless specified otherwise.

Protocol Aqueous Solubility Assay

Assay Name: Thermodynamic Equilibrium Aqueous Solubility Assay

Description: The purpose of this assay is to provide a medium throughput estimation of the thermodynamic equilibrium aqueous solubility of compounds at room temperature. Solvent system default is 50 mM pH 6.5 potassium phosphate buffer.

Detailed Protocol:

Standards Preparation—The calibration standard is prepared by accurately weighing 0.5-0.7 mg of sample in 5 ml of methanol. If the material is not fully soluble in methanol, other solvents such as DMSO or mixed solvents will be used. (*The calibration standard is typically prepared fresh immediately before the start of the assay.

** Note the calibration standard must be fully dissolved.)

A two-point calibration curve should be used to determine the concentration of the final solution. A serial dilution is performed on the standard solution.

Test Sample Preparation—

The final saturated solution is prepared by adding 1.0 ml of the appropriate aqueous solvent to the remaining portion of material (1 dram submission vial). The solution is sonicated and vortexed for ~30 seconds. The sample solution is placed on an orbiter that continually agitates the sample solutions for 15-24 hours at room temperature. The final saturated solution is then transferred to a 1.5 ml eppendorf tube and centrifuged for ~2 min. at 10000 rpms. The supernatant from the saturated solution is transferred to a glass HPLC-suitable vial without filtering since the 1.5 ml volume is insufficient to saturate the syringe filter. This sample preparation procedure nullifies the effects of non-specific binding to the filtering apparatus.

LC Quantitation—

The standards and sample are analyzed by HPLC using either UV/Vis diode array or variable wavelength detection. Typical quantitation wavelengths are 210 or 254 nm; detection wavelength can be individually customized to optimize sensitivity. In addition to UV detection, mass spectrometry detection is recommended if available in order to confirm the identity of the HPLC-UV peak of interest.

Dilutions of aqueous test solutions are performed if HPLC-UV peak is beyond the linear portion of the standard calibration curve. Typical dilutions include 100 ul/900 ul (×10) or 500 ul/500 ul (2 ×), as required.

Reagents —HPLC grade solvents are employed

Data and Explanation of Table 1—

Table 1 shows the superiority of the compounds of this invention as a selected subgroup of the earlier case U.S. application Ser. No. 11/454,324, filed on Jun. 16, 2006 and published on Dec. 21, 2006 (WO2006/138682, published on Dec. 28, 2006), referenced above. Compounds of the present invention demonstrate unexpected combination of high CB-1 inverse agonist activity and a short canine half-life, or have increased aqueous solubility of >1 µg/mL achieved by the combination of appropriate $Ar_1$, $Ar_2$ and $R_1$ The compounds of the instant invention preferably have CB-1 Ki values of 0.5 nM-20 nM with and canine half-life values of <50 hrs or have increased aqueous solubility of >1 µg/mL.

| Example No. | Structure | CB1 Ki | Solubility (mg/ml) | Canine half life |
|---|---|---|---|---|
| 17 | 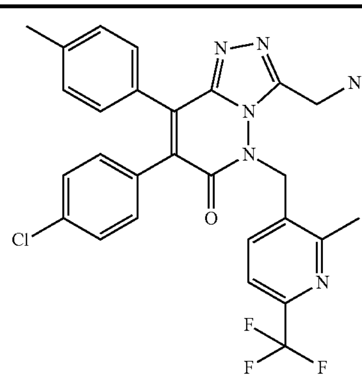 | 20 | | 31 |

| Example No. | Structure | CB1 Ki | Solubility (mg/ml) | Canine half life |
|---|---|---|---|---|
| 6 | 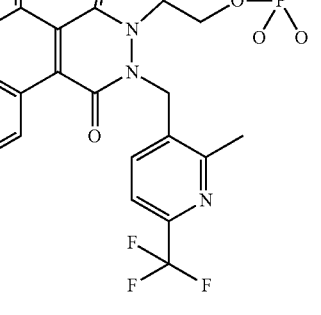 | | | prodrug of Example 3 |
| 9 | 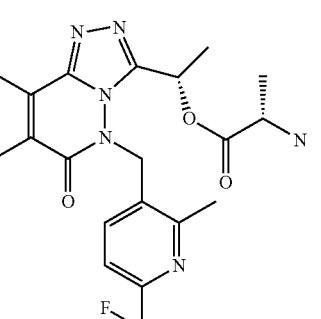 | | | prodrug of Example 23 |
| 18 | 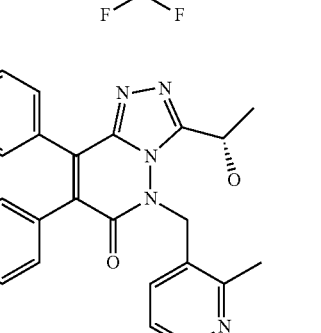 | 14 | 7 | |
| 8 | 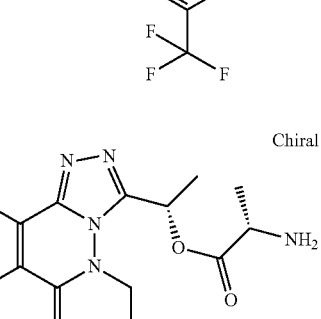 Chiral | | | prodrug of 24 |

-continued

| Example No. | Structure | CB1 Ki | Solubility (mg/ml) | Canine half life |
|---|---|---|---|---|
| 16 | 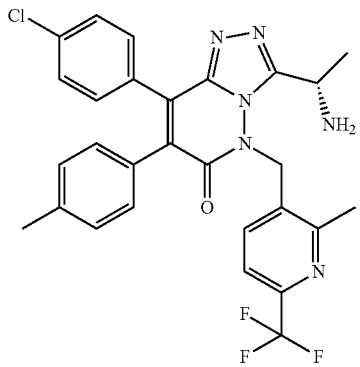 | 6 | 38 | |
| 19 | 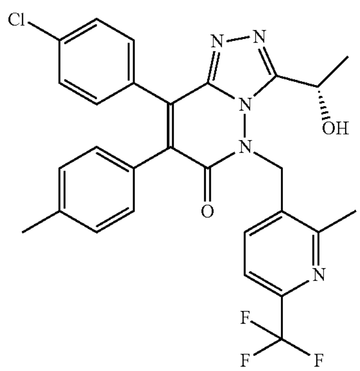 | 5 | 7 | |
| 7 | (Chiral) | prodrug | | |
| 13 | 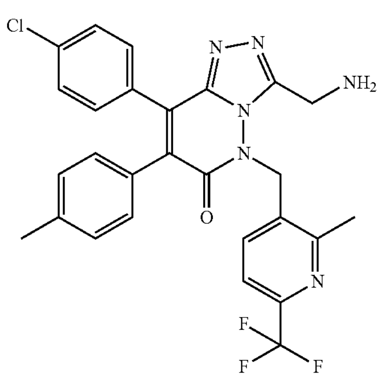 | 3 | 20 | |

-continued

| Example No. | Structure | CB1 Ki | Solubility (mg/ml) | Canine half life |
| --- | --- | --- | --- | --- |
| 21 | 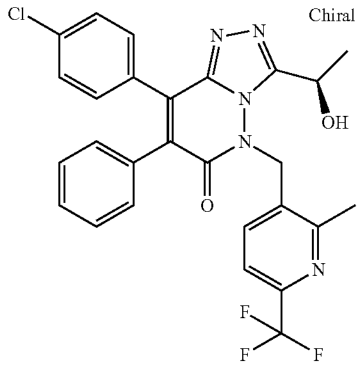 | 27 | 31 | |
| 14 | 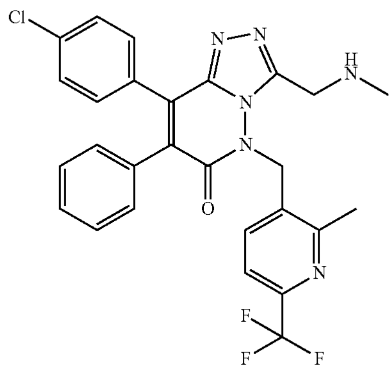 | 10 | 25 | |
| 20 | 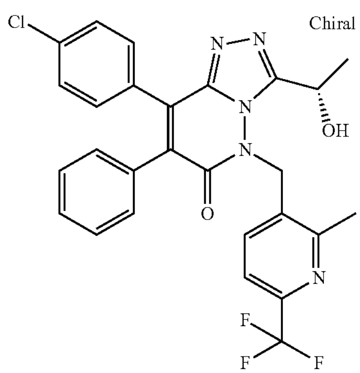 | 6 | 22 | |
| 12 | 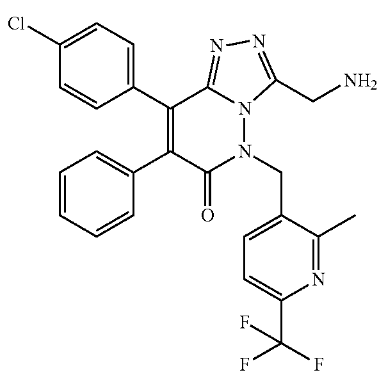 | 8 | 101 | |

-continued
| Example No. | Structure | CB1 Ki | Solubility (mg/ml) | Canine half life |
| --- | --- | --- | --- | --- |
| 22 | 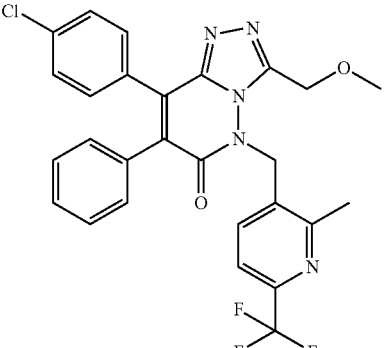 | 3 | 4 | 39 |
| 15 | 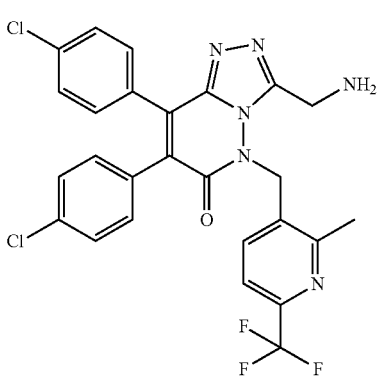 | 12 | 16 | |
| 5 | 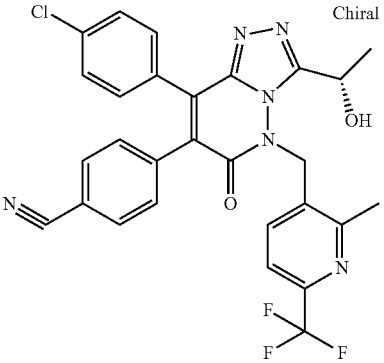 Chiral | 10 | | |
| 11 | 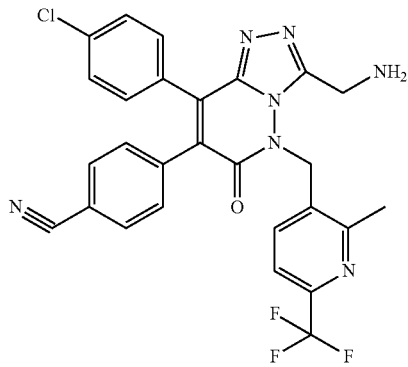 | 11 | | |

-continued

| Example No. | Structure | CB1 Ki | Solubility (mg/ml) | Canine half life |
|---|---|---|---|---|
| 4 | 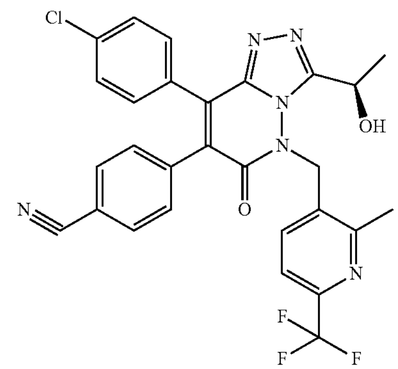 | 15 | 10 | |
| 10 | 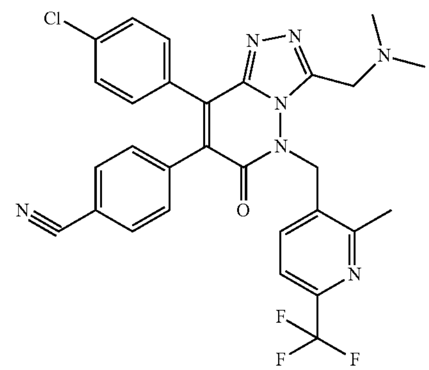 | 13 | 2 | |
| 3 | 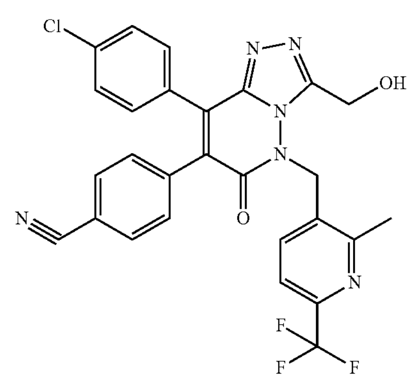 | 3 | 15 | 20 |
| 2 | 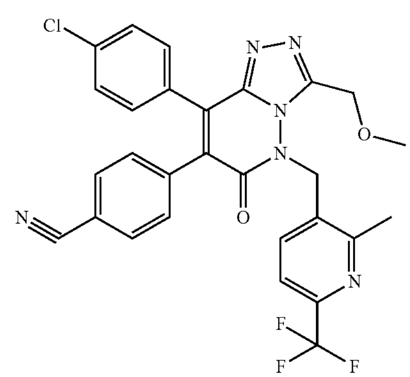 | 5 | 6 | 23 |

Utilities and Combinations

Utilities

The compounds of the present invention are cannabinoid receptor modulators, and include compounds which are, for example, selective agonists, partial agonists, inverse agonists, antagonists or partial antagonists of the cannabinoid receptor. Accordingly, the compounds of the present invention may be useful for the treatment or prevention of diseases and disorders associated with G-protein coupled cannabinoid receptor activity. Preferably, compounds of the present invention possess activity as antagonists or inverse agonists of the CB-1 receptor, and may be used in the treatment of diseases or disorders associated with the activity of the CB-1 receptor.

Accordingly, the compounds of the present invention can be administered to mammals, preferably humans, for the treatment of a variety of conditions and disorders, including, but not limited to metabolic and eating disorders as well as conditions associated with metabolic disorders, (e.g., obesity, diabetes, arteriosclerosis, hypertension, polycystic ovary disease, cardiovascular disease, osteoarthritis, dermatological disorders, hypertension, insulin resistance, hypercholesterolemia, hypertriglyceridemia, cholelithiasis and sleep disorders, hyperlipidemic conditions, bulimia nervosa and compulsive eating disorders) or psychiatric disorders, such as substance abuse, depression, anxiety, mania and schizophrenia. These compounds could also be used for the improvement of cognitive function (e.g., the treatment of dementia, including Alzheimer's disease, short term memory loss and attention deficit disorders); neurodegenerative disorders (e.g., Parkinson's Disease, cerebral apoplexy and craniocerebral trauma) and hypotension (e.g., hemorrhagic and endotoxin-inducd hypotension). These compounds could also be used for treatment of catabolism in connection with pulmonary dysfunction and ventilator dependency; treatment of cardiac dysfunction (e.g., associated with valvular disease, myocardial infarction, cardiac hypertrophy or congestive heart failure); and improvement of the overall pulmonary function; transplant rejection; rheumatoid arthritis; multiple sclerosis; inflammatory bowel disease; lupus; graft vs. host disease; T-cell mediated hypersensitivity disease; psoriasis; asthma; Hashimoto's thyroiditis; Guillain-Barre syndrome; cancer; contact dermatitis; allergic rhinitis; and ischemic or reperfusion injury.

Compounds useful in the treatment of appetitive or motivational disorders regulate desires to consume sugars, carbohydrates, alcohol or drugs and more generally to regulate the consumption of ingredients with hedonic value. In the present description and in the claims, appetitive disorders are understood as meaning: disorders associated with a substance and especially abuse of a substance and/or dependency on a substance, disorders of eating behaviors, especially those liable to cause excess weight, irrespective of its origin, for example: bulimia nervosa, craving for sugars. The present invention therefore further relates to the use of a CB-1 receptor antagonist or inverse agonist for the treatment of bulimia and obesity, including obesity associated with type II diabetes (non-insulin-dependent diabetes), or more generally any disease resulting in the patient becoming overweight. Obesity, as described herein, is defined by a body mass index ($kg/m^2$) of at least 26. It may be due to any cause, whether genetic or environmental, including overeating and bulimia, polycycstic ovary disease, craniopharyngeoma, Prader-Willi Syndrome, Frohlich's Syndrome, Type II diabetes, growth hormone deficiency, Turner's Syndrome and other pathological states characterized by reduced metabolic activity or reduced energy expenditure. As used with reference to the utilities described herein, the term "treating" or "treatment" encompasses prevention, partial alleviation, or cure of the disease or disorder. Further, treatment of obesity is expected to prevent progression of medical covariants of obesity, such as arteriosclerosis, Type II diabetes, polycystic ovary disease, cardiovascular disease, osteoarthritis, dermatological disorders, hypertension, insulin resistance, hypercholesterolemia, hypertriglyceridemia, cholelithiasis and sleep disorders.

Compounds in the present invention may also be useful in treating substance abuse disorders, including substance dependence or abuse without physiological dependence. Substances of abuse include alcohol, amphetamines (or amphetamine-like substances), caffeine, cannabis, cocaine, hallucinogens, inhalants, nicotine, opioids, phencyclidine (or phencyclidine-like compounds), sedative-hypnotics or benzodiazepines, and other (or unknown) substances and combinations of the above. The terms "substance abuse disorders" also includes drug or alcohol withdrawal syndromes and substance-induced anxiety or mood disorder with onset during withdrawal.

Compounds in the present invention may be useful in treating memory impairment and cognitive disorders. The condition of memory impairment is manifested by impairment of the ability to learn new information and/or the inability to recall previously learned information. Memory impairment is a primary symptom of dementia and can also be a symptom associated with such diseases as Alzheimer's disease, schizophrenia, Parkinson's disease, Huntington's disease, Pick's disease, Creutzfeld-Jakob disease, HIV, cardiovascular disease, and head trauma as well as age-related cognitive decline. Dementias are diseases that include memory loss and additional intellectual impairment separate from memory. Cannabinoid receptor modulators may also be useful in treating cognitive impairments related to attentional deficits, such as attention deficit disorder.

Compounds in the present invention may also be useful in treating diseases associated with dysfunction of brain dopaminergic systems, such as Parkinson's Disease and substance abuse disorders. Parkinsons's Disease is a neurodenerative movement disorder characterized by bradykinesia and tremor.

As modulators of the cannabinoid receptor, the compounds of the present invention are further useful for the treatment and prevention of respiratory diseases and disorders. Respiratory diseases for which cannabinoid receptor modulators are useful include, but are not limited to, chronic pulmonary obstructive disorder, emphysema, asthma, and bronchitis. In addition, cannabinoid receptor modulators block the activation of lung epithelial cells by moieties such as allergic agents, inflammatory cytokines or smoke, thereby limiting release of mucin, cytokines, and chemokines, or selectively inhibiting lung epithelial cell activation.

Moreover, the compounds employed in the present invention may stimulate inhibitory pathways in cells, particularly in leukocytes, lung epithelial cells, or both, and are thus useful in treating such diseases. "Leukocyte activation" is defined herein as any or all of cell proliferation, cytokine production, adhesion protein expression, and production of inflammatory mediators. "Epithelial cell activation" is defined herein as the production of any or all of mucins, cytokines, chemokines, and adhesion protein expression.

Use of the compounds of the present invention for treating leukocyte activation-associated disorders is exemplified by, but is not limited to, treating a range of disorders such as: transplant (such as organ transplant, acute transplant, xenotransplant or heterograft or homograft (such as is employed in burn treatment)) rejection; protection from ischemic or reperfusion injury such as ischemic or reperfusion injury incurred during organ transplantation, myocardial infarction, stroke or other causes; transplantation tolerance induction; arthritis (such as rheumatoid arthritis, psoriatic arthritis or osteoarthritis); multiple sclerosis; respiratory and pulmonary diseases including but not limited to chronic obstructive pulmonary disease (COPD), emphysema, bronchitis, and acute respiratory distress syndrome (ARDS); inflammatory bowel disease, including ulcerative colitis and Crohn's disease; lupus (systemic lupus erythematosis); graft vs. host disease; T-cell mediated hypersensitivity diseases, including contact hypersensitivity, delayed-type hypersensitivity, and gluten-sensitive enteropathy (Celiac disease); psoriasis; contact dermatitis (including that due to poison ivy); Hashimoto's thyroiditis; Sjogren's syndrome; Autoimmune Hyperthyroidism, such as Graves' Disease; Addison's disease (autoimmune disease of the adrenal glands); Autoimmune polyglandular disease (also known as autoimmune polyglandular syndrome); autoimmune alopecia; pernicious anemia; vitiligo; autoimmune hypopituatarism; Guillain-Barre syndrome; other autoimmune diseases; glomerulonephritis; serum sickness; uticaria; allergic diseases such as respiratory allergies (asthma, hay fever, allergic rhinitis) or skin allergies; scleracierma; mycosis fungoides; acute inflammatory and respiratory responses (such as acute respiratory distress syndrome and ishchemia/reperfusion injury); dermatomyositis; alopecia greata; chronic actinic dermatitis; eczema; Behcet's disease; Pustulosis palmoplanteris; Pyoderma gangrenum; Sezary's syndrome; atopic dermatitis; systemic schlerosis; and morphea. The term "leukocyte activation-associated" or "leukocyte-activation mediated" disease as used herein includes each of the above referenced diseases or disorders. In a particular embodiment, the compounds of the present invention are useful for treating the aforementioned exemplary disorders irrespective of their etiology. The combined activity of the present compounds towards monocytes, macrophages, T-cells, etc. may be useful in treating any of the above-mentioned disorders.

Cannabinoid receptors are important in the regulation of Fc gamma receptor responses of monocytes and macrophages. Compounds of the present invention inhibit the Fc gamma dependent production of TNF alpha in human monocytes/macrophages. The ability to inhibit Fc gamma receptor dependent monocyte and macrophage responses results in additional anti-inflammatory activity for the present compounds. This activity is especially of value, for example, in treating inflammatory diseases such as arthritis or inflammatory bowel disease. In particular, the present compounds are useful for treating autoimmune glomerulonephritis and other instances of glomerulonephritis induced by deposition of immune complexes in the kidney that trigger Fc gamma receptor responses leading to kidney damage.

Cannabinoid receptors are expressed on lung epithelial cells. These cells are responsible for the secretion of mucins and inflammatory cytokines/chemokines in the lung and are thus intricately involved in the generation and progression of respiratory diseases. Cannabinoid receptor modulators regulate both the spontaneous and the stimulated production of both mucins and cytokines. Thus, such compounds are useful in treating respiratory and pulmonary diseases including, COPD, ARDS, and bronchitis.

Further, cannabinoid receptors may be expressed on gut epithelial cells and hence regulate cytokine and mucin production and may be of clinical use in treating inflammatory diseases related to the gut. Cannabinoid receptors are also expressed on lymphocytes, a subset of leukocytes. Thus, cannabinoid receptor modulators will inhibit B and T-cell activation, proliferation and differentiation. Thus, such compounds will be useful in treating autoimmune diseases that involve either antibody or cell mediated responses such as multiple sclerosis and lupus.

In addition, cannabinoid receptors regulate the Fc epsilon receptor and chemokine induced degranulation of mast cells and basophils. These play important roles in asthma, allergic rhinitis, and other allergic disease. Fc epsilon receptors are stimulated by IgE-antigen complexes. Compounds of the present invention inhibit the Fc epsilon induced degranulation responses, including the basophil cell line, RBL. The ability to inhibit Fc epsilon receptor dependent mast cell and basophil responses results in additional anti-inflammatory and anti-allergic activity for the present compounds. In particular, the present compounds are useful for treating asthma, allergic rhinitis, and other instances of allergic disease.

Combinations

The present invention includes within its scope pharmaceutical compositions comprising, as an active ingredient, a therapeutically effective amount of at least one of the compounds of formula I, alone or in combination with a pharmaceutical carrier or diluent. Optionally, compounds of the present invention can be used alone, in combination with other suitable therapeutic agents useful in the treatment of the aforementioned disorders including: anti-obesity agents; anti-diabetic agents, appetite suppressants; cholesterol/lipid-lowering agents, HDL-raising agents, cognition enhancing agents, agents used to treat neurodegeneration, agents used to treat respiratory conditions, agents used to treat bowel disorders, anti-inflammatory agents; anti-anxiety agents; anti-depressants; anti-hypertensive agents; cardiac glycosides; and anti-tumor agents.

Such other therapeutic agent(s) may be administered prior to, simultaneously with, or following the administration of the cannabinoid receptor modulators in accordance with the invention.

Examples of suitable anti-obesity agents for use in combination with the compounds of the present invention include melanocortin receptor (MC4R) agonists, melanin-concentrating hormone receptor (MCHR) antagonists, growth hormone secretagogue receptor (GHSR) antagonists, galanin receptor modulators, orexin antagonists, CCK agonists, GLP-1 agonists, and other Pre-proglucagon-derived peptides; NPY1 or NPY5 antagonsist, NPY2 and NPY4 modulators, corticotropin releasing factor agonists, histamine receptor-3 (H3) modulators, aP2 inhibitors, PPAR gamma modulators, PPAR delta modulators, acetyl-CoA carboxylase (ACC) inihibitors, 11-β-HSD-1 inhibitors, adinopectin receptor modulators; beta 3 adrenergic agonists, such as AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, a thyroid receptor beta modulator, such as a thyroid receptor ligand as disclosed in WO 97/21993 (U. Cal SF), WO 99/00353 (KaroBio) and WO 00/039077 (KaroBio), a lipase inhibitor, such as orlistat or ATL-962 (Alizyme), serotonin receptor agonists, (e.g., BVT-933 (Biovitrum)), monoamine reuptake inhibitors or releasing agents, such as fenfluramine, dexfenfluramine, fluvoxamine, fluoxetine, paroxetine, sertraline, chlorphentermine, cloforex, clortermine, picilorex, sibutramine, dexamphetamine, phentermine, phenylpropanolamine or mazindol, anorectic agents such as topiramate (Johnson & Johnson), CNTF (ciliary neurotrophic factor)/Axokine® (Regeneron), BDNF (brain-derived neurotrophic factor), leptin and leptin receptor modulators, or cannabinoid-1 receptor antagonists, such as SR-141716 (Sanofi) or SLV-319 (Solvay).

Examples of suitable anti-diabetic agents for use in combination with the compounds of the present invention include: insulin secretagogues or insulin sensitizers, which may include biguanides, sulfonyl ureas, glucosidase inhibitors, aldose reductase inhibitors, PPAR γ agonists such as thiazolidinediones, PPAR α agonists (such as fibric acid derivatives), PPAR δ antagonists or agonists, PPAR α/γ dual agonists, 11-β-HSD-1 inhibitors, dipeptidyl peptidase IV (DP4) inhibitors, SGLT2 inhibitors, glycogen phosphorylase inhibitors, and/or meglitinides, as well as insulin, and/or glucagon-like peptide-1 (GLP-1), GLP-1 agonist, and/or a PTP-1B inhibitor (protein tyrosine phosphatase-1B inhibitor).

The antidiabetic agent may be an oral antihyperglycemic agent preferably a biguanide such as metformin or phenformin or salts thereof, preferably metformin HCl. Where the antidiabetic agent is a biguanide, the compounds of the present invention will be employed in a weight ratio to biguanide within the range from about 0.001:1 to about 10:1, preferably from about 0.01:1 to about 5:1.

The antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the beta-cells, with glyburide and glipizide being preferred, which may be administered in the same or in separate oral dosage forms. The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of the present invention may be employed in combination with a PPAR γ agonist such as a thiazolidinedione oral anti-diabetic agent or other insulin sensitizers (which has an insulin sensitivity effect in NIDDM patients) such as rosiglitazone (SKB), pioglitazone (Takeda), Mitsubishi's MCC-555 (disclosed in U.S. Pat. No. 5,594,016), Glaxo-Wellcome's GL-262570, englitazone (CP-68722, Pfizer) or darglitazone (CP-86325, Pfizer, isaglitazone (MIT/J&J), JTT-501 (JPNT/P&U), L-895645 (Merck), R-119702 (Sankyo/WL), N,N-2344 (Dr. Reddy/NN), or YM-440 (Yamanouchi), preferably rosiglitazone and pioglitazone.

The compounds of the present invention may be employed with a PPARα/γ dual agonist such as MK-767/KRP-297 (Merck/Kyorin; as described in, K. Yajima, et. al., Am. J. Physiol. Endocrinol. Metab., 284: E966-E971 (2003)), AZ-242 (tesaglitazar; Astra-Zeneca; as described in B. Ljung, et. al., J. Lipid Res., 43, 1855-1863 (2002)); muraglitazar; or the compounds described in U.S. Pat. No. 6,414,002.

The compounds of the present invention may be employed in combination with anti-hyperlipidemia agents, or agents used to treat arteriosclerosis. An example of an hypolipidemic agent would be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, pitavastatin (Nissan/Sankyo's nisvastatin (NK-104) or itavastatin), disclosed in U.S. Pat. No. 5,011,930, Shionogi-Astra/Zeneca rosuvastatin (visastatin (ZD-4522)) disclosed in U.S. Pat. No. 5,260,440, and related statin compounds disclosed in U.S. Pat. No. 5,753,675, pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl)pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No. 0,142,146A2, and quinoline and pyridine derivatives disclosed in U.S. Pat. Nos. 5,506,219 and 5,691,322. In addition, phosphinic acid compounds useful in inhibiting HMG CoA reductase suitable for use herein are disclosed in GB 2205837.

The squalene synthetase inhibitors suitable for use herein include, but are not limited to, α-phosphono-sulfonates disclosed in U.S. Pat. No. 5,712,396, those disclosed by Biller, et al., J. Med. Chem., 31, 1869-1871 (1998) including isoprenoid (phosphinyl-methyl)phosphonates as well as other known squalene synthetase inhibitors, for example, as disclosed in U.S. Pat. Nos. 4,871,721 and 4,924,024 and in Biller, S. A., Neuenschwander, K., Ponpipom, M. M., and Poulter, C. D., Current Pharmaceutical Design, 2, 1-40 (1996).

In addition, other squalene synthetase inhibitors suitable for use herein include the terpenoid pyrophosphates disclosed by P. Ortiz de Montellano, et al., J. Med. Chem., 20, 243-249 (1977), the farnesyl diphosphate analog A and presqualene pyrophosphate (PSQ-PP) analogs as disclosed by Corey and Volante, J. Am. Chem. Soc., 98, 1291-1293 (1976), phosphinylphosphonates reported by McClard, R. W. et al., J. Am. Chem. Soc., 109, 5544 (1987) and cyclopropanes reported by Capson, T. L., PhD dissertation, June, 1987, Dept. Med. Chem. U of Utah, Abstract, Table of Contents, pp 16, 17, 40-43, 48-51, Summary.

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (SEC-HOLEX, POLICEXIDE) and cholestagel (Sankyo/Geltex), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid (niacin), acipimox, acifran, neomycin, p-aminosalicylic acid, aspirin, poly(diallylmethylamine) derivatives such as disclosed in U.S. Pat. No. 4,759,923, quaternary amine poly (diallyldimethylammonium chloride) and ionenes such as disclosed in U.S. Pat. No. 4,027,009, and other known serum cholesterol lowering agents.

The other hypolipidemic agent may be an ACAT inhibitor (which also has anti-atherosclerosis activity) such as disclosed in, Drugs of the Future, 24, 9-15 (1999), (Avasimibe); "The ACAT inhibitor, Cl-1011 is effective in the prevention and regression of aortic fatty streak area in hamsters", Nicolosi et al., Atherosclerosis (Shannon, Irel), 137(1), 77-85 (1998); "The pharmacological profile of FCE 27677: a novel ACAT inhibitor with potent hypolipidemic activity mediated by selective suppression of the hepatic secretion of ApoB100-containing lipoprotein", Ghiselli, Giancarlo, Cardiovasc. Drug Rev., 16 (1), 16-30 (1998); "RP 73163: a bioavailable alkylsulfinyl-diphenylimidazole ACAT inhibitor", Smith, C., et al., Bioorg. Med. Chem. Lett, 6 (1), 47-50 (1996); "ACAT inhibitors: physiologic mechanisms for hypolipidemic and anti-atherosclerotic activities in experimental animals", Krause et al., Editor(s): Ruffolo, Robert R., Jr.; Hollinger, Mannfred A., Inflammation: Mediators Pathways, 173-98 (1995), Publisher: CRC, Boca Raton, Fla.; "ACAT inhibitors: potential anti-atherosclerotic agents", Sliskovic et al., Curr. Med. Chem., 1 (3), 204-25 (1994); "Inhibitors of acyl-CoA: cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)-methyl]ureas with enhanced hypocholesterolemic activity", Stout et al., Chemtracts: Org. Chem., 8 (6), 359-62 (1995), or TS-962 (Taisho Pharmaceutical Co. Ltd), as well as F-1394, CS-505, F-12511, HL-004, K-10085 and YIC-C8-434.

The hypolipidemic agent may be an upregulator of LDL receptor activity such as MD-700 (Taisho Pharmaceutical Co. Ltd) and LY295427 (Eli Lilly). The hypolipidemic agent may be a cholesterol absorption inhibitor preferably Schering-Plough's SCH48461 (ezetimibe) as well as those disclosed in Atherosclerosis 115, 45-63 (1995) and J. Med. Chem. 41, 973 (1998).

The other lipid agent or lipid-modulating agent may be a cholesteryl transfer protein inhibitor (CETP) such as Pfizer's CP-529,414 as well as those disclosed in WO/0038722 and in EP 818448 (Bayer) and EP 992496, and Pharmacia's SC-744 and SC-795, as well as CETi-1 and JTT-705.

The hypolipidemic agent may be an ileal Na$^+$/bile acid cotransporter inhibitor such as disclosed in Drugs of the Future, 24, 425-430 (1999). The ATP citrate lyase inhibitor which may be employed in the combination of the invention may include, for example, those disclosed in U.S. Pat. No. 5,447,954.

The other lipid agent also includes a phytoestrogen compound such as disclosed in WO 00/30665 including isolated soy bean protein, soy protein concentrate or soy flour as well as an isoflavone such as genistein, daidzein, glycitein or equol, or phytosterols, phytostanol or tocotrienol as disclosed in WO 2000/015201; a beta-lactam cholesterol absorption inhibitor such as disclosed in EP 675714; an HDL upregulator such as an LXR agonist, a PPAR α-agonist and/or an FXR agonist; an LDL catabolism promoter such as disclosed in EP 1022272; a sodium-proton exchange inhibitor such as disclosed in DE 19622222; an LDL-receptor inducer or a steroidal glycoside such as disclosed in U.S. Pat. No. 5,698,527 and GB 2304106; an anti-oxidant such as beta-carotene, ascorbic acid, α-tocopherol or retinol as disclosed in WO 94/15592 as well as Vitamin C and an antihomocysteine agent such as folic acid, a folate, Vitamin B6, Vitamin B12 and Vitamin E; isoniazid as disclosed in WO 97/35576; a cholesterol absorption inhibitor, an HMG-CoA synthase inhibitor, or a lanosterol demethylase inhibitor as disclosed in WO 97/48701; a PPAR δ agonist for treating dyslipidemia; or a sterol regulating element binding protein-I (SREBP-1) as disclosed in WO 2000/050574, for example, a sphingolipid, such as ceramide, or neutral sphingomyelenase (N-SMase) or fragment thereof. Preferred hypolipidemic agents are pravastatin, lovastatin, simvastatin, atorvastatin, fluvastatin, pitavastatin and rosuvastatin, as well as niacin and/or cholestagel.

The compounds of the present invention may be employed in combination with anti-hypertensive agents. Examples of suitable anti-hypertensive agents for use in combination with the compounds of the present invention include beta adrenergic blockers, calcium channel blockers (L-type and/or T-type; e.g. diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043, 265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

Cannbinoid receptor modulators could be useful in treating other diseases associated with obesity, including sleep disorders. Therefore, the compounds described in the present invention could be used in combination with therapeutics for treating sleep disorders. Examples of suitable therapies for treatment of sleeping disorders for use in combination with the compounds of the present invention include melatonin analogs, melatonin receptor antagonists, ML 1 B agonists, GABA receptor modulators; NMDA receptor modulators, histamine-3 (H3) receptor modulators, dopamine agonists and orexin receptor modulators.

Cannabinoid receptor modulators may reduce or ameliorate substance abuse or addictive disorders. Therefore, combination of cannabinoid receptor modulators with agents used to treat addictive disorders may reduce the dose requirement or improve the efficacy of current addictive disorder therapeutics. Examples of agents used to treat substance abuse or addictive disorders are: selective serotonin reuptake inhibitors (SSRI), methadone, buprenorphine, nicotine and bupropion.

Cannabinoid receptor modulators may reduce anxiety or depression; therefore, the compounds described in this application may be used in combination with anti-anxiety agents or antidepressants. Examples of suitable anti-anxiety agents for use in combination with the compounds of the present invention include benzodiazepines (e.g., diazepam, lorazepam, oxazepam, alprazolam, chlordiazepoxide, clonazepam, chlorazepate, halazepam and prazepam), 5HT1A receptor agonists (e.g., buspirone, flesinoxan, gepirone and ipsapirone), and corticotropin releasing factor (CRF) antagonists.

Examples of suitable classes of anti-depressants for use in combination with the compounds of the present invention include norepinephrine reuptake inhibitors (tertiary and secondary amine tricyclics), selective serotonin reuptake inhibitors (SSRIs) (fluoxetine, fluvoxamine, paroxetine and sertraline), monoamine oxidase inhibitors (MAOIs) (isocarboxazid, phenelzine, tranylcypromine, selegiline), reversible inhibitors of monoamine oxidase (RIMAs) (moclobemide), serotonin and norepinephrine reuptake inhibitors (SNRIs) (venlafaxine), corticotropin releasing factor (CRF) receptor antagonists, alpah-adrenoreceptor antagonists, and atypical antidepressants (bupropion, lithium, nefazodone, trazodone and viloxazine).

The combination of a conventional antipsychotic drug with a CB-1 receptor antagonist could also enhance symptom reduction in the treatment of psychosis or mania. Further, such a combination could enable rapid symptom reduction, reducing the need for chronic treatment with antipsychotic agents. Such a combination could also reduce the effective antipsychotic dose requirement, resulting in reduced probability of developing the motor dysfunction typical of chronic antipsychotic treatment.

Examples of suitable antipsychotic agents for use in combination with the compounds of the present invention include the phenothiazine (chlorpromazine, mesoridazine, thioridazine, acetophenazine, fluphenazine, perphenazine and trifluoperazine), thioxanthine (chlorprothixene, thiothixene), heterocyclic dibenzazepine (clozapine, olanzepine and aripiprazole), butyrophenone (haloperidol), dipheyylbutylpiperidine (pimozide) and indolone (molindolone) classes of antipsychotic agents. Other antipsychotic agents with potential therapeutic value in combination with the compounds in the present invention include loxapine, sulpiride and risperidone.

Combination of the compounds in the present invention with conventional antipsychotic drugs could also provide an enhanced therapeutic effect for the treatment of schizophrenic disorders, as described above for manic disorders. As used here, schizophrenic disorders include paranoid, disorganized, catatonic, undifferentiated and residual schizophrenia, schizophreniform disorder, shcizoaffective disorder, delusional disorder, brief psychotic disorder and psychotic disorder not specified. Examples of suitable antipsychotic drugs for combination with the compounds in the present invention include the antipsychotics mentioned above, as well as dopamine receptor antagonists, muscarinic receptor agonists, 5HT2A receptor antagonists and 5HT2A/dopamine receptor antagonists or partial agonists (e.g., olanzepine, aripiprazole, risperidone, ziprasidone).

The compounds described in the present invention could be used to enhance the effects of cognition-enhancing agents, such as acetylcholinesterase inhibitors (e.g., tacrine), muscarinic receptor-1 agonists (e.g., milameline), nicotinic agonists, glutamic acid receptor (AMPA and NMDA) modulators, and nootropic agents (e.g., piracetam, levetiracetam). Examples of suitable therapies for treatment of Alzheimer's disease and cognitive disorders for use in combination with the compounds of the present invention include donepezil, tacrine, revastigraine, 5HT6, gamma secretase inhibitors, beta secretase inhibitors, SK channel blockers, Maxi-K blockers, and KCNQs blockers.

The compounds described in the present invention could be used to enhance the effects of agents used in the treatment of Parkinson's Disease. Examples of agents used to treat Parkinson's Disease include: levadopa with or without a COMT inhibitor, antiglutamatergic drugs (amantadine, riluzole), alpha-2 adrenergic antagonists such as idazoxan, opiate antagonists, such as naltrexone, other dopamine agonists or transportor modulators, such as ropinirole, or pramipexole or neurotrophic factors such as glial derived neurotrophic factor (GDNF).

The compounds described in the present invention could be used in combination with suitable anti-inflammatory agents. Examples of suitable anti-inflammatory agents for use in combination with the compounds of the present invention include prednisone, dexamethasone, cyclooxygenase inhibitors (i.e., COX-1 and/or COX-2 inhibitors such as NSAIDs, aspirin, indomethacin, ibuprofen, piroxicam, NAPROXEN®, CELEBREX®, VIOXX®), CTLA4-Ig agonists/antagonists, CD40 ligand antagonists, IMPDH inhibitors, such as mycophenolate (CELLCEPT®), integrin antagonists, alpha-4beta-7integrin antagonists, cell adhesion inhibitors, interferon gamma antagonists, ICAM-1, tumor necrosis factor (TNF) antagonists (e.g., infliximab, OR1384, including TNF-alpha inhibitors, such as tenidap, anti-TNF antibodies or soluble TNF receptor such as etanercept (ENBREL®), rapamycin (sirolimus or Rapamune) and leflunomide (Arava)), prostaglandin synthesis inhibitors, budesonide, clofazimine, CNI-1493, CD4 antagonists (e.g., priliximab), p38 mitogen-activated protein kinase inhibitors, protein tyrosine kinase (PTK) inhibitors, IKK inhibitors, and therapies for the treatment of irritable bowel syndrome (e.g., ZELNORM® and MAXI-K® openers such as those disclosed in U.S. Pat. No. 6,184,231 B1).

Exemplary of such other therapeutic agents which may be used in combination with cannabinoid receptor modulators include the following: cyclosporins (e.g., cyclosporin A), anti-IL-2 receptor (Anti-Tac), anti-CD45 RB, anti-CD2, anti-CD3(OKT-3), anti-CD4, anti-CD80, anti-CD86, monoclonal antibody OKT3, agents blocking the interaction between CD40 and gp39, such as antibodies specific for CD40 and/or gp39 (i.e., CD154), fusion proteins constructed from CD40 and gp39 (CD40 Ig and CD8 gp39), inhibitors, such as nuclear translocation inhibitors, of NF-kappa B function, such as deoxyspergualin (DSG), gold compounds, antiproliferative agents such as methotrexate, FK506 (tacrolimus, Prograf), mycophenolate mofetil, cytotoxic drugs such as azathiprine and cyclophosphamide, anticytokines such as antiIL-4 or IL-4 receptor fusion proteins and PDE 4 inhibitors such as Ariflo, and the PTK inhibitors disclosed in the following U.S. patent applications, incorporated herein by reference in their entirety: Ser. No. 09/097,338, filed Jun. 15, 1998; Ser. No. 09/094,797, filed Jun. 15, 1998; Ser. No. 09/173,413, filed Oct. 15, 1998; and Ser. No. 09/262,525, filed Mar. 4, 1999. See also the following documents and references cited therein and incorporated herein by reference: Hollenbaugh, D., et al., "Cleavable CD40Ig Fusion Proteins and the Binding to Sgp39", *J. Immunol. Methods* (Netherlands), 188 (1), pp. 1-7 (Dec. 15, 1995); Hollenbaugh, D., et al., "The Human T Cell Antigen Gp39, A Member of the TNF Gene Family, Is a Ligand for the CD40 Receptor: Expression of a Soluble Form of Gp39with B Cell Co-Stimulatory Activity", *EMBO J* (England), 11 (12), pp. 4313-4321 (December 1992); and Moreland, L. W. et al., "Treatment of Rheumatoid Arthritis with a Recombinant Human Tumor Necrosis Factor Receptor (P75)-Fc Fusion Protein," *New England J. of Medicine,* 337 (3), pp. 141-147 (1997).

The above other therapeutic agents, when employed in combination with the compounds of the present invention, may be used, for example, in those amounts indicated in the *Physicians' Desk Reference* (PDR) or as otherwise determined by one of ordinary skill in the art.

The compounds of formula (I) of the invention can be administered orally or parenterally, such as subcutaneously or intravenously, as well as by nasal application, rectally or sublingually to various mammalian species known to be subject to such maladies, e.g., humans, in an effective amount up to 1 gram, preferably up to 200 mg, more preferably up to 100 mg in a regimen of single, two or four divided daily doses.

The compounds of the formula (I) can be administered for any of the uses described herein by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents. The present compounds can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps. The present compounds can also be administered liposomally.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate and/or lactose and/or other excipients, binders, extenders, disintegrants, diluents and lubricants such as those known in the art. The compounds of formula I can also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use.

Exemplary compositions for nasal aerosol or inhalation administration include solutions in saline which can contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono-or diglycerides, and fatty acids, including oleic acid, or Cremaphor.

Exemplary compositions for rectal administration include suppositories which can contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

It will be understood that the specific dose level and frequency of dosage for any particular subject can be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition.

It should be understood that while this invention has been described herein in terms of specific embodiments set forth in detail, such embodiments are presented by way of illustration of the general principles of the invention, and the invention is not necessarily limited thereto. Certain modifications and variations in any given material, process step or chemical formula will be readily apparent to those skilled in the art without departing from the true spirit and scope of the present invention, and all such modifications and variations should be considered within the scope of the claims that follow.

What is claimed is:
1. A compound according to Formula Ia:

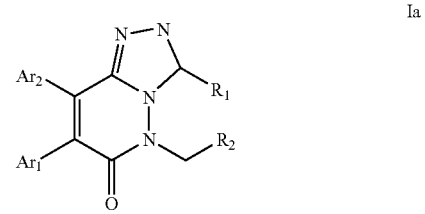

or a pharmaceutically acceptable salt or a stereoisomer thereof,
wherein:
Ar$_1$ is aryl, which may be optionally substituted with 1-3 members selected from the group consisting of halogen, haloalkyl, cyano, alkyl, alkoxy, and haloalkoxy;
Ar$_2$ is aryl, which may be optionally substituted with 1-3 members selected from the group consisting of halogen, haloalkyl, cyano, alkyl, alkoxy, and haloalkoxy;
R$_1$ is alkyl, wherein the alkyl group is substituted with either an —OR$_4$ or an —NR$_5$R$_6$ group;
R$_2$ is selected from the group consisting of aryl and heteroaryl, wherein the aryl and heteroaryl may each be optionally substituted with 1-2 members selected from the group consisting of halogen, alkyl, haloalkyl, cyano, cycloalkyl, and alkoxy;
R4 is selected from the group consisting of hydrogen, alkyl, haloalkyl, and phosphates;
R$_5$ and R$_6$ are each independently selected from the group consisting of hydrogen and alkyl, wherein the alkyl may be optionally substituted with 1-3 halogen; or
R$_5$ and R$_6$ may be taken together with the nitrogen to which they are attached to form a heterocyclyl ring forming a 4, 5, 6, or 7 membered rings.
2. The compound according to claim 1, wherein:
Ar$_1$ is phenyl optionally substituted with 1-3 members selected from the group consisting chloro, fluoro, trifluoromethyl, cyano, methyl, ethyl, methoxy, trifluoromethoxy and difluromethoxy;
Ar$_2$ is phenyl optionally substituted with 1-3 members selected from the group consisting of chloro, fluoro, trifluoromethyl, cyano, methyl, ethyl, methoxy, trifluoromethoxy and difluromethoxy;
R$_1$ is selected from the group consisting of methyl, ethyl and isopropyl, and is substituted with either an —OR$_4$ or an —NR$_5$R$_6$ group;
R$_2$ is selected from the group consisting of phenyl, 2-pyridyl and 3-pyridyl, each of which is optionally substituted with 1-2 members selected from the group consisting of fluoro, chloro, methyl, ethyl, propyl, isopropyl, trifluoromethyl, difluoromethyl, cyano, cyclopropyl, cylobutyl, methoxy and ethoxy;

$R_4$ is selected from the group consisting of hydrogen, methyl, ethyl, trifluoromethyl, difluoromethyl, —PO$_3$Na$_2$ and —PO$_3$HNa;

$R_5$ and $R_6$ are each independently selected from the group consisting of hydrogen, methyl and ethyl, wherein the methyl and ethyl may be optionally substituted with 1-3 halogen; or $R_5$ and $R_6$ may be taken together with the nitrogen to which they are attached to form a heterocyclyl ring forming a 4, 5, 6, or 7 membered rings.

3. A compound according to claim 1 wherein:
$R_1$ is a methyl, ethyl or isopropyl group which is substituted with an —OR$_4$ or —NR$_5$R$_6$ group;
$R_4$ is selected from the group consisting of hydrogen, methyl, ethyl, isopropyl, and phosphate;
$R_5$ and $R_6$ are each independently selected from the group consisting of hydrogen, methyl, ethyl, propyl and isopropyl; or
$R_5$ and $R_6$ together with the nitrogen to which they are attached form a 4, 5, 6, or 7-membered ring having 1 nitrogen and the remainder of the ring members as carbon.

4. A compound according to claim 1 wherein:
$R_2$ is selected from the group consisting of 2-pyridinyl, and 3-pyridinyl, which may be optionally substituted with 1-3 members selected from the group consisting of chloro, fluoro, methyl, ethyl, isopropyl, cyclopropyl, cyclobutyl, trifluoromethyl, cyano, and hydroxymethyl.

5. A compound according to claim 1 wherein:
Ar$_1$ is selected from the group consisting of phenyl optionally substituted with methyl, trifluoromethyl, chloro, fluoro or cyano;
Ar$_2$ is selected from the group consisting of phenyl optionally substituted with methyl, methoxy, trifluoromethyl, chloro, fluoro or cyano;
$R_1$ is selected from the group consisting of —CH$_2$OR$_4$, —CH(CH$_3$)OR$_4$, —C(CH$_3$)$_2$OR$_4$, —CH$_2$CH$_2$OR$_4$, —CH$_2$NR$_5$R$_6$, —CH(CH$_3$)NR$_5$R$_6$ and —C(CH$_3$)$_2$NR$_5$R$_6$;
$R_2$ is selected from the group consisting of pheny, 2-pyridyl and 3-pyridyl, wherein the pheny, 2-pyridyl and 3-pyridyl may each be optionally substituted with 1-2 members selected from the group consisting of fluoro, chloro, methyl, ethyl, propyl, isopropyl, trifluoromethyl, difluoromethyl, cyano, cycloproplyl, cylobutyl, methoxy and ethoxy;
$R_4$ is selected from the group consisting of hydrogen, methyl ethyl, and —P(O)(OH)$_2$;
$R_5$ and $R_6$ are each independently selected from the group consisting of hydrogen and methyl.

6. A compound according to claim 1 wherein:
$R_2$ is selected from the group consisting of:
(a) phenyl substituted with cyano;
(b) pyridyl substituted with 1-2 members selected from the group consisting of methyl, ethyl, isopropyl, and trifluoromethyl.

7. A compound according to claim 6 wherein $R_2$ is selected from the group consisting of 4-cyanophenyl, 4-trifluoromethyl-2-pyridyl, 4-trifluoromethy-3-pyridyl, 2-methyl-4-trifluoromethy-3-pyridyl, 2-ethyl-4-trifluoromethy-3-pyridyl, and 2-isopropyl-4-trifluoromethyl-3-pyridyl.

8. A compound according to claim 1 wherein $R_4$ is —P(O)(OH)(ONa) or —P(O)(ONa)$_2$.

9. The compound according to claim 1, wherein:
Ar$_1$ is substituted and is selected from the group consisting of 4-chlorophenyl, 4-cyanophenyl and 4-fluorophenyl;
Ar$_2$ is substituted and is selected from the group consisting of phenyl, 4-chlorophenyl, 4-cyanophenyl, 4-fluorophenyl, 4-methylphenyl, and 4-methoxyphenyl;
$R_1$ is selected from the group consisting of —CH$_2$OR$_4$, —CH(CH$_3$)OR$_4$, —C(CH$_3$)$_2$OR4, —CH$_2$CH$_2$OR$_4$, —CH$_2$NR$_5$R$_6$, —CH(CH$_3$)NR$_5$R$_6$ and —C(CH$_3$)$_2$NR$_5$R$_6$;
$R_2$ is substituted and is selected from the group consisting of 4-cyanophenyl, 4-trifluoromethy-2-pyridyl, 4-trifluoromethy-3-pyridyl, 2-methyl-4-trifluoromethy-3-pyridyl, 4,4'-difluorocyclohexyl, 4-trifluoromethyl-cyclohexyl, bicyclo[2.2.1]heptyl, 3-trifluomethyl-isoxazolyl, 4-trifluoromethyl-phenyl;
$R_4$ is selected from the group consisting of hydrogen, methyl and —P(O)(OH)$_2$;
$R_5$ and $R_6$ are each independently selected from the group consisting of hydrogen and methyl.

10. A pharmaceutical composition, comprising a compound according to claim 1 and a pharmaceutically acceptable carrier or diluent.

11. A pharmaceutical composition comprising a compound according to claim 1 and an additional therapeutic agent.

12. A compound according to claim 1 selected from group consisting of

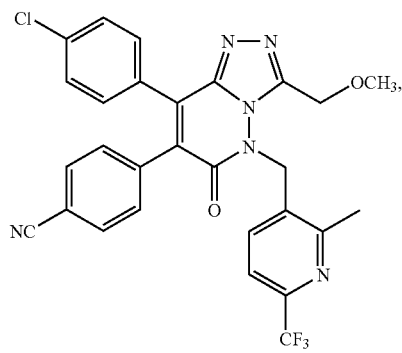

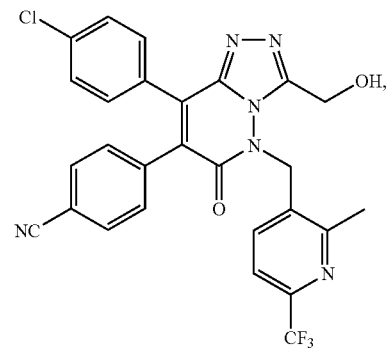

67
-continued
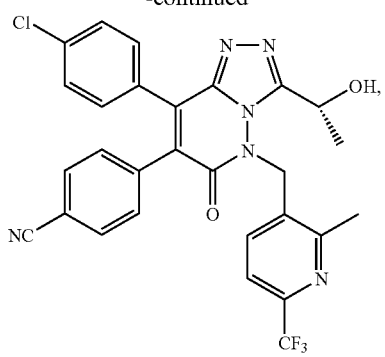
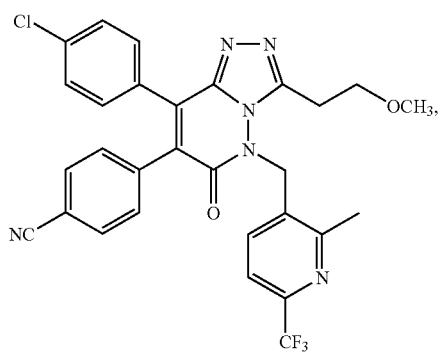
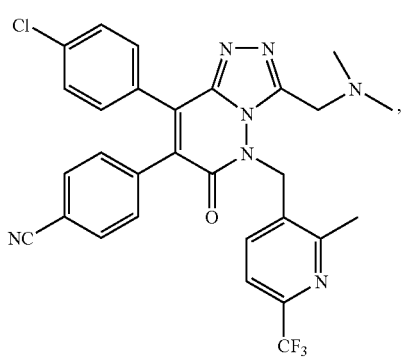
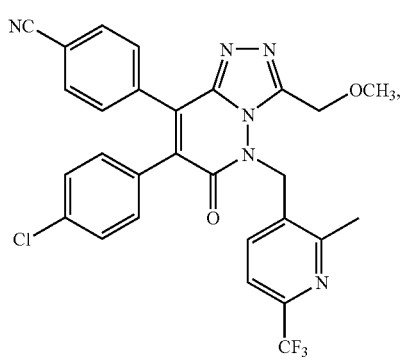
68
-continued
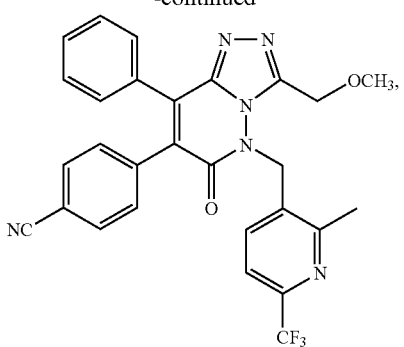
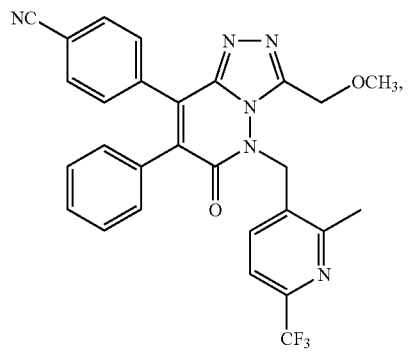
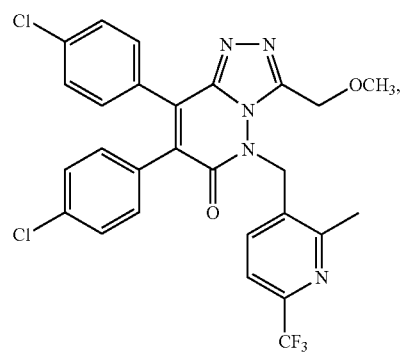
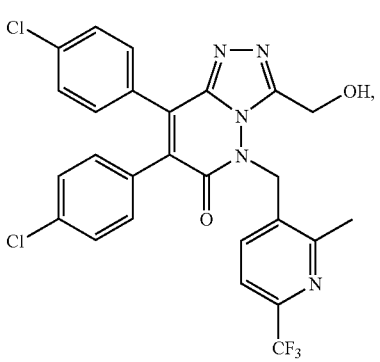

69
-continued
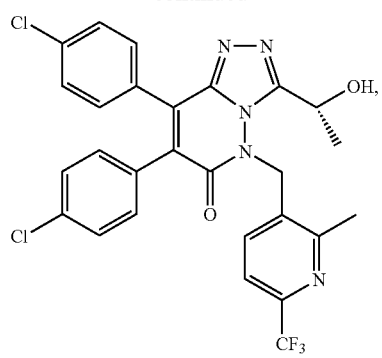
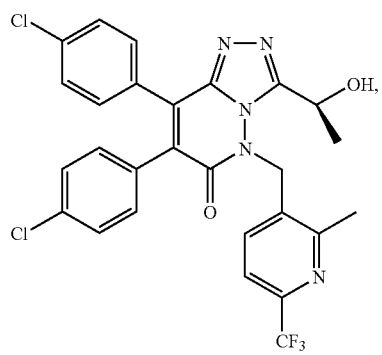
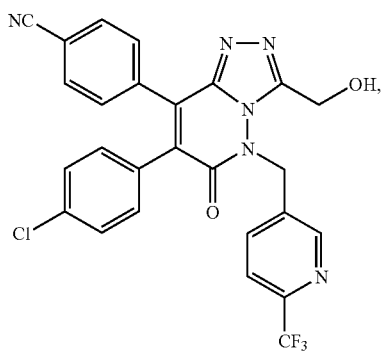
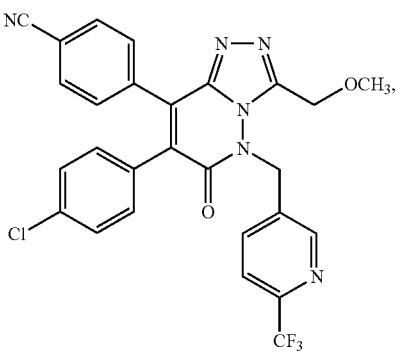
70
-continued
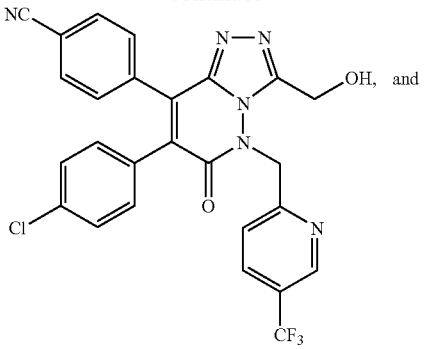
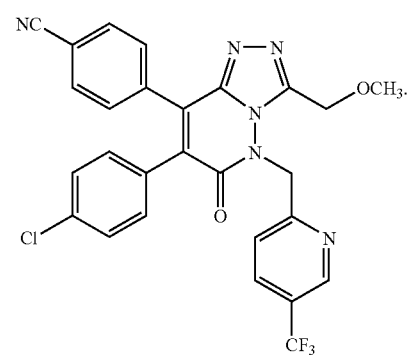
13. A compound according to claim 12 selected from group consisting of:
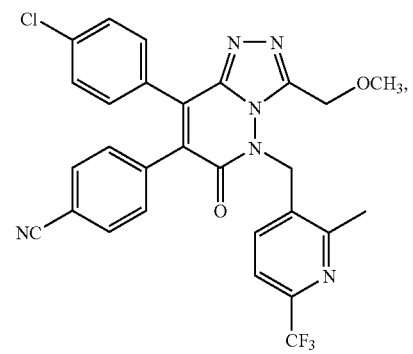
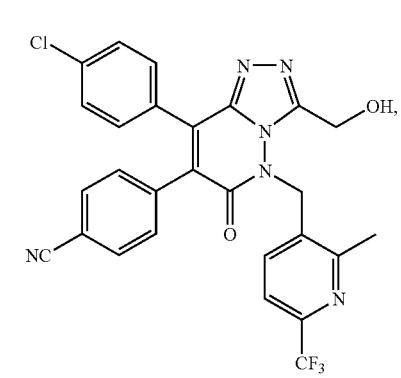

71
-continued
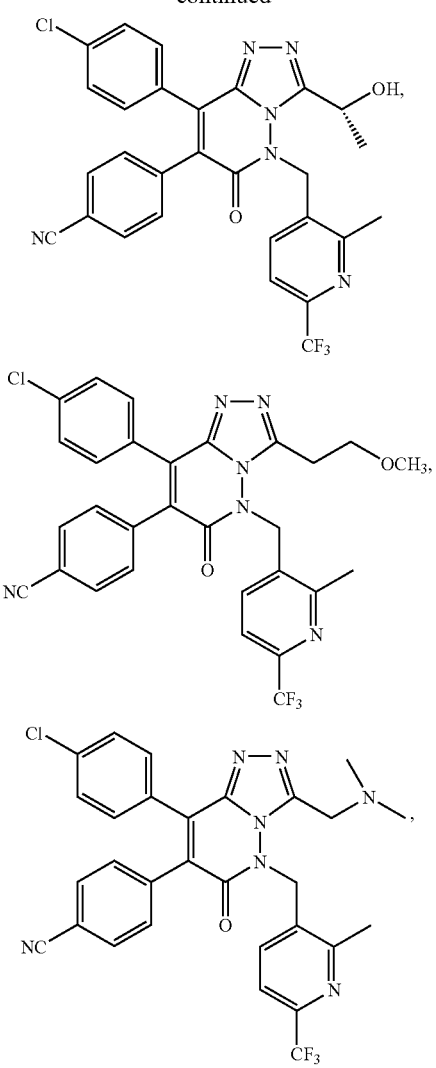
72
-continued
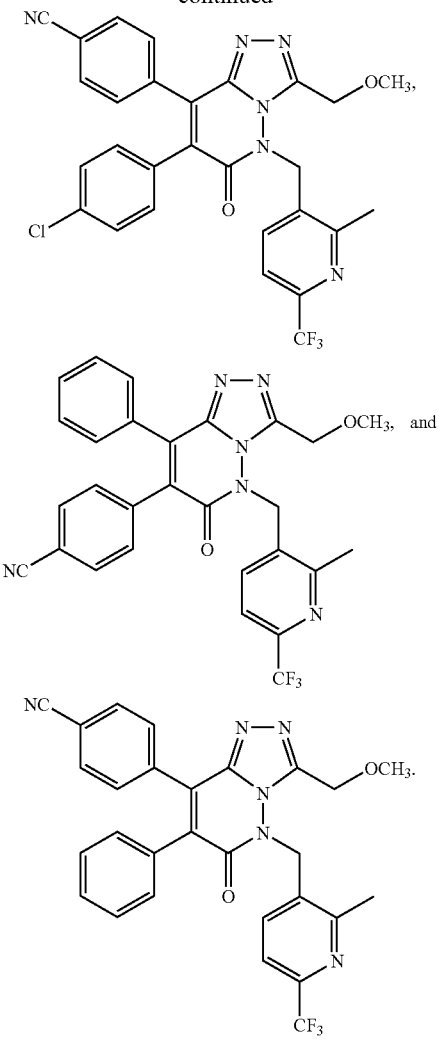
* * * * *

UNITED STATES PATENT AND TRADEMARK OFFICE
CERTIFICATE OF CORRECTION

PATENT NO. : 8,030,306 B2
APPLICATION NO. : 12/518707
DATED : October 4, 2011
INVENTOR(S) : William R. Ewing et al.

It is certified that error appears in the above-identified patent and that said Letters Patent is hereby corrected as shown below:

Claim 1:

Column 64, lines 19 to 26, change

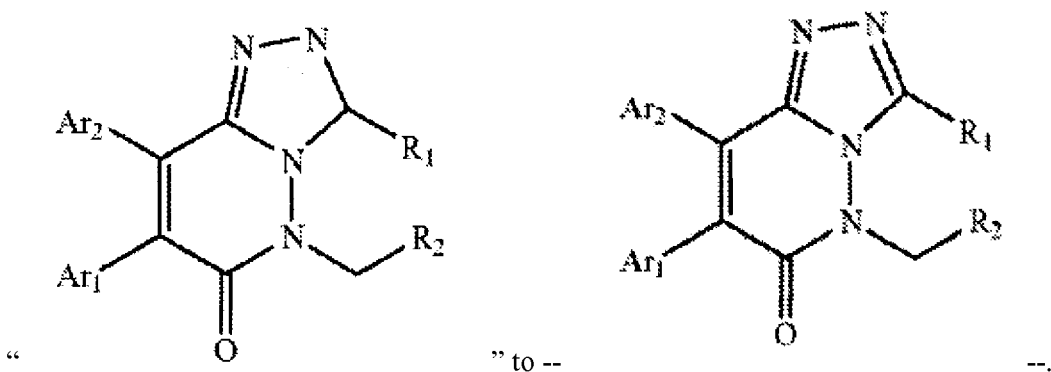

Column 64, line 44, change "R4" to -- $R_4$ --.

Claim 2:

Column 64, line 56, change "difluromethoxy" to -- difluoromethoxy --.

Column 64, line 60, change "difluromethoxy" to -- difluoromethoxy --.

Column 65, line 2, change "cylobutyl" to -- cyclobutyl --.

Claim 5:

Column 65, line 44, change "pheny" to -- phenyl --.

Column 65, line 45, change "pheny" to -- phenyl --.

Column 65, line 49, change "cycloproplyl, cylobutyl," to -- cyclopropyl, cyclobutyl, --.

Column 65, line 52, after "methyl", insert -- , --.

Signed and Sealed this
Thirty-first Day of July, 2012

David J. Kappos
*Director of the United States Patent and Trademark Office*

CERTIFICATE OF CORRECTION (continued)
U.S. Pat. No. 8,030,306 B2

Claim 7:

Column 65, line 63, change "trifluoromethy" to -- trifluoromethyl --.

Column 65, lines 63 and 64, change "trifluoromethy" to -- trifluoromethyl --.

Column 65, line 64, change "trifluoromethy" to -- trifluoromethyl --.

Claim 9:

Column 66, line 9, change "—C(CH$_3$)$_2$OR4," to -- —C(CH$_3$)$_2$OR$_4$, --.

Column 66, line 14, change "trifluoromethy" to -- trifluoromethyl --.

Column 66, lines 14 and 15, change "trifluoromethy" to -- trifluoromethyl --.

Column 66, line 15, change "trifluoromethy" to -- trifluoromethyl --.

Column 66, line 17, change "trifluomethyl" to -- trifluoromethyl --.

Claim 12:

Column 66, line 32, after "of", insert -- : --.